United States Patent
Andersen et al.

(10) Patent No.: US 6,677,147 B2
(45) Date of Patent: *Jan. 13, 2004

(54) PECTATE LYASES

(75) Inventors: Lene Nonboe Andersen, Allerod (DK); Martin Schülein, late of Copenhagen (DK), legal representative Hanne Dela; Niels Erik Krebs Lange, Raleigh, NC (US); Mads Eskelund Bjørnvad, Frederiksberg (DK); Søren Møller, Holte (DK); Sanne O. Schroder Glad, Ballerup (DK); Markus Sakari Kauppinen, Copenhagen N (DK); Kirk Schnorr, Copenhagen N (DK); Lars Kongsbak, Holte (DK)

(73) Assignee: Novozymes A/S, Bagsvaerd (DK)

( * ) Notice: Subject to any disclaimer, the term of this patent is extended or adjusted under 35 U.S.C. 154(b) by 85 days.

This patent is subject to a terminal disclaimer.

(21) Appl. No.: 10/072,152

(22) Filed: Feb. 7, 2002

(65) Prior Publication Data

US 2002/0142438 A1 Oct. 3, 2002

Related U.S. Application Data

(63) Continuation of application No. 09/694,531, filed on Oct. 23, 2000, now Pat. No. 6,368,843, which is a continuation of application No. 09/198,955, filed on Nov. 24, 1998, now Pat. No. 6,187,580, which is a continuation-in-part of application No. 09/073,684, filed on May 6, 1998, now Pat. No. 6,124,127, and a continuation-in-part of application No. 09/184,217, filed on Nov. 2, 1998, now Pat. No. 6,258,590.

(60) Provisional application No. 60/067,240, filed on Dec. 2, 1997, and provisional application No. 60/067,249, filed on Dec. 2, 1997.

(51) Int. Cl.[7] ................................................. C12N 9/88
(52) U.S. Cl. .................................................... 435/232
(58) Field of Search ................................. 435/232, 183, 435/252.3, 252.33, 262, 263, 264, 267; 510/300; 530/23.2

(56) References Cited

FOREIGN PATENT DOCUMENTS

EP 0 870 834 A1 10/1998
WO WO 98/45393 10/1998

OTHER PUBLICATIONS

Abstract Derwent Accession No. 81–54142D [25] JP 56068393.
Nasser et al., (1990) Biochimie 72:689–695.
Karbassi et al., (1980) Can. J. Microbiol. 26: 377–384.
Kelly et al., (1978) Can. J. Microbiol. 24:1164–1172.
Kim et al., (1994) Biosci. Biotech. Biochem 58(5):947–949.
Nasser et al., (1993) FEBS 13343, 335(3):319–326.
Guevara et al., (1997) Can. J. Microbiol. 43:245–253.
Kopecny et al., (1995) Letter in Applied Microbiol. 20: 312–316.
Yoshimitsu Miyazaki (1991) Agric. Biol. Chem. 55(1): 25–30.
File WPI, Derwent accession No. 90–28 5860.
STN International, File CA, Chem. Abst. vol. 118 Abst. No. 250 320.
File WPI, Derwent Accession No. 88–209811.
EMBL, Database Genbank, Accession No. L41673.

*Primary Examiner*—Nashaat T. Nashed
(74) *Attorney, Agent, or Firm*—Elias J. Lambiris

(57) ABSTRACT

The present invention relates to pectate lyases comprising the amino acid sequence Asn Leu Asn Ser Arg Val Pro (NLNSRVP) (SEQ ID NO: 2) belonging to Family 1 of polysaccharide lyases have good performance in industrial processes under neutral or alkaline conditions such as laundering and textile processing. The pectate lyase may be derivable from Bacillus species.

13 Claims, 3 Drawing Sheets

```
            1
SEQ ID NO:2   ......AASN QPTSNGPQGY ASMNGGTTGG AGGRVEYAST GAQIQQLIDN
SEQ ID NO:4   ASALNSGKVN PLADFSLKGF AALNGGTTGG EGGQTVTVTT GDQLIAALKN
SEQ ID NO:6   .......... ..DFSKPLGY ASMNGGTTGG QGGRVEYAST GSQLQKLIDD
SEQ ID NO:10  ...KGESDST MNADFSMQGF ATLNGGTTGG AGGQTVVST GDELLAALKN
SEQ ID NO:8   .......... NTPNENLQGF ATLNGGTTGG AGGDVVTVRT GNELINALKS

51
SEQ ID NO:2   RSRSNNPDEP LTIYVNGTIT QGNSPQSLID VKNHRGKAHE IKNISIIGVG
SEQ ID NO:4   K....NANTP LKIYVNGTIT TSNTSASKID VK.......D VSNVSIVGSG
SEQ ID NO:6   RSRSNNPNQP LTIYVTGKIT LQNSSDDKIE VKNHRGQAHE IRNLSIIGQG
SEQ ID NO:8   K....NSNTP LTIYVNGTIT PSNTSASKID IK.......D VNDVSILGVG
SEQ ID NO:10  K....NPNRP LTIYVNGTIT PNNTSDSKID IK.......D VSNVSILGVG

101
SEQ ID NO:2   TNGEFDGIGI RLSNAHNIII QNVSIHHVRE G...EGTAIE VTDESKNVWI
SEQ ID NO:4   TKGELKGIGI KIWRANNIII RNLKIHEVAS GDK...DAIG IEGPSKNIWV
SEQ ID NO:6   TRGEFDGIGL RLINAHNVIV RNLSIHHVRA GSG.EGTSIE VTQGSKNIWI
SEQ ID NO:8   TQGEFNGIGI KVWRANNIIL RNLKIHHVNT GDK...DAIS IEGPSKNIWV
SEQ ID NO:10  TNGRLNGIGI KVWRANNIII RNLTIHEVHT GDKDAISMIS IEGPSRNIWV

151
SEQ ID NO:2   DHNEFYSEFP GNGDSDYYDG LVDIKRNAEY ITVSWNKFEN HWKTMLVGHT
SEQ ID NO:4   DHNELYHSLN ..VDKDYYDG LFDVKRDAEY ITFSWNYVHD GWKSMLMGSS
SEQ ID NO:6   DHNEFYSQLD GNNNPDLYDG LVDIKRNSEY ITVSWNKFEN HWKTMLVGHT
SEQ ID NO:8   DHNELYNSLD ..VHKDYYDG LFDVKRDADY ITFSWNYVHD SWKSMLMGSS
SEQ ID NO:10  DHNELYASLN ..VHKDHYDG LFDVKRDAYN ITFSWNYVHD GWKAMLMGNS

201
SEQ ID NO:2   DNASLAPDKI TYHHNYFNNL NSRVPLIRYA DVHMFNNYFK DINDTAINSR
SEQ ID NO:4   D.SDNYNRTI TFHHNWFENL NSRVPSFRFG EGHIYNNYFN KIIDSGINSR
SEQ ID NO:6   DNASLAPDKV TYHHNFFHNL NSRVPLIRFA DVHMVNNYFK DIKDTAINSR
SEQ ID NO:8   D.SDSYNRKI TFHNNYFENL NSRVPSIRFG EAHIFSNYYN GINETGINSR
SEQ ID NO:10  D.SDNYDRNI TFHHNYFKNL NSRVPAYRFG KAHLFSNYFE NILETGINSR

251
SEQ ID NO:2   VGARVEVENN YFDNVGSGQA DPTTGFIKGP VGWFYGSPST GYWNLRGNVF
SEQ ID NO:4   MGARIRIENN LFENAKD... ..........P IVSWY.SSSP GYWHVSNNKF
SEQ ID NO:6   MGARVFVENN YFENVGSGQQ DPTTRQIKTA VGWFYGSSST GYWNLRGNQF
SEQ ID NO:8   MGAKVRIEEN LFERANN... ..........P IVSRD.SRQV GYWHLINNHF
SEQ ID NO:10  MGAEMLVEHN VFENATN... ..........P LGFWH.SSRT GYWNVANNRY 301                                              344
SEQ ID NO:2   VN.TPNSHLS STTNFTPPYS YKVQSATQAK SSVEQHSGVG VIN.
SEQ ID NO:4   VNSRGSMPTT STTYNPPYS  YSLDNVDNVK SIVKQNAGVG KINP
SEQ ID NO:6   IN.TPSSHLS STTTFTPPYQ FNAQSAQDAK QAVEGFSGVG VVQ.
SEQ ID NO:8   TQSTGEIPTT STITYNPPYS YQATPVGQVK DVVRANAGVG KVTG
SEQ ID NO:10  INSTGSMPTT STTNYRPPYP YTVTPVGDVK SVVTRYAGVG VIQP
```

FIG 1

SEQUENCE LISTING

<160> NUMBER OF SEQ ID NOS: 32

<210> SEQ ID NO 1
<211> LENGTH: 1077
<212> TYPE: DNA
<213> ORGANISM: B. agaradherens

<400> SEQUENCE: 1

```
atgactaaag tctttaaatt gttactggca ttagctctcg ttttaccagt tatctcattt      60
agttctcctg cctcgcaagc tgcttcaaat cagccaactt ctaacggacc acaaggctat     120
gcgtcaatga atggagggac aaccggtggt gcaggcggcc gtgtcgaata tgcaagcacc     180
ggagcgcaaa ttcagcaatt gatagataat cgcagccgaa gtaataaccc tgatgaacca     240
ttaacgattt atgtaaacgg aacgattaca caaggaaatt ccccacagtc ccttatagat     300
gttaaaaatc accgtggaaa agctcatgaa attaaaaaca tctctattat cggtgtagga     360
acaaatggag agtttgatgg cattgggata agactatcaa acgcccataa tatcattatc     420
```

```
caaaatgtat caattcatca tgtgcgagag ggagaaggca cggctattga agtgacagat    480
gagagtaaaa acgtgtggat cgatcacaac gagttttata gtgaatttcc aggtaatgga    540
gactcagatt attacgatgg tctcgtagac ataaaaagaa acgctgaata tattacggtt    600
tcatggaata agtttgagaa tcattggaaa acgatgctcg tcggtcatac tgataatgcc    660
tcattagcgc cagataaaat tacgtaccat cacaattatt ttaataatct taattcacgt    720
gtcccgctta ttcgatacgc tgatgttcca atgttcaata actattttaa agacattaac    780
gatacagcga ttaacagtcg tgtaggggcc cgtgtctttg tagaaaacaa ctattttgac    840
aacgtaggat caggacaagc tgacccaacg actggtttta ttaaagggcc tgttggttgg    900
ttctatggaa gtccgagtac tggatattgg aatttacgtg gaaatgtatt tgttaataca    960
ccgaatagtc atttaagctc tacaacaaac tttacaccac catatagtta caaagtccaa   1020
tcagctaccc aagctaagtc gtcggttgaa caacattcgg gagtaggtgt tatcaac     1077

<210> SEQ ID NO 2
<211> LENGTH: 359
<212> TYPE: PRT
<213> ORGANISM: B. agaradherens

<400> SEQUENCE: 2

Met Thr Lys Val Phe Lys Leu Leu Leu Ala Leu Ala Leu Val Leu Pro
 1               5                  10                  15

Val Ile Ser Phe Ser Ser Pro Ala Ser Gln Ala Ala Ser Asn Gln Pro
             20                  25                  30

Thr Ser Asn Gly Pro Gln Gly Tyr Ala Ser Met Asn Gly Gly Thr Thr
         35                  40                  45

Gly Gly Ala Gly Gly Arg Val Glu Tyr Ala Ser Thr Gly Ala Gln Ile
     50                  55                  60

Gln Gln Leu Ile Asp Asn Arg Ser Arg Ser Asn Asn Pro Asp Glu Pro
65                  70                  75                  80

Leu Thr Ile Tyr Val Asn Gly Thr Ile Thr Gln Gly Asn Ser Pro Gln
                 85                  90                  95

Ser Leu Ile Asp Val Lys Asn His Arg Gly Lys Ala His Glu Ile Lys
            100                 105                 110

Asn Ile Ser Ile Ile Gly Val Gly Thr Asn Gly Glu Phe Asp Gly Ile
        115                 120                 125

Gly Ile Arg Leu Ser Asn Ala His Asn Ile Ile Gln Asn Val Ser
    130                 135                 140

Ile His His Val Arg Glu Gly Glu Gly Thr Ala Ile Glu Val Thr Asp
145                 150                 155                 160

Glu Ser Lys Asn Val Trp Ile Asp His Asn Glu Phe Tyr Ser Glu Phe
                165                 170                 175

Pro Gly Asn Gly Asp Ser Asp Tyr Tyr Asp Gly Leu Val Asp Ile Lys
            180                 185                 190

Arg Asn Ala Glu Tyr Ile Thr Val Ser Trp Asn Lys Phe Glu Asn His
        195                 200                 205

Trp Lys Thr Met Leu Val Gly His Thr Asp Asn Ala Ser Leu Ala Pro
    210                 215                 220

Asp Lys Ile Thr Tyr His His Asn Tyr Phe Asn Asn Leu Asn Ser Arg
225                 230                 235                 240

Val Pro Leu Ile Arg Tyr Ala Asp Val His Met Phe Asn Asn Tyr Phe
                245                 250                 255
```

Lys Asp Ile Asn Asp Thr Ala Ile Asn Ser Arg Val Gly Ala Arg Val
                260                 265                 270

Phe Val Glu Asn Asn Tyr Phe Asp Asn Val Gly Ser Gly Gln Ala Asp
                275                 280                 285

Pro Thr Thr Gly Phe Ile Lys Gly Pro Val Gly Trp Phe Tyr Gly Ser
                290                 295                 300

Pro Ser Thr Gly Tyr Trp Asn Leu Arg Gly Asn Val Phe Val Asn Thr
305                 310                 315                 320

Pro Asn Ser His Leu Ser Ser Thr Thr Asn Phe Thr Pro Pro Tyr Ser
                325                 330                 335

Tyr Lys Val Gln Ser Ala Thr Gln Ala Lys Ser Ser Val Glu Gln His
                340                 345                 350

Ser Gly Val Gly Val Ile Asn
        355

<210> SEQ ID NO 3
<211> LENGTH: 1026
<212> TYPE: DNA
<213> ORGANISM: Bacillus licheniformis - ATCC 14580

<400> SEQUENCE: 3
atgaagaaat taatcagcat catctttatc tttgtattag gggttgtcgg gtcattgaca      60
gcggcggttt cggcagaagc agcttctgcc ttaaactcgg gcaaagtaaa tccgcttgcc     120
gacttcagct taaaaggctt tgccgcacta acggcggaa caacgggcgg agaaggcggt      180
cagacggtaa ccgtaacaac gggagatcag ctgattgcgg cattaaaaaa taagaatgca     240
aatacgcctt taaaaattta tgtcaacggc accattacaa catcaaatac atccgcatca     300
aagattgacg tcaaagacgt gtcaaacgta tcgattgtcg gatcagggac caaggggaa      360
ctcaaaggga tcggcatcaa atatggcgg gccaacaaca tcatcatccg caacttgaaa      420
attcacgagg tcgcctcagg cgataaagac gcgatcggca ttgaaggccc ttctaaaaac     480
atttgggttg atcataatga gctttaccac agcctgaacg ttgacaaaga ttactatgac     540
ggattatttg acgtcaaaag agatgcggaa tatattacat tctcttggaa ctatgtgcac     600
gatggatgga atcaatgct gatgggttca tcggacagcg ataattacaa caggacgatt      660
acattccatc ataactggtt tgagaatctg aattcgcgtg tgccgtcatt ccgtttcgga     720
gaaggccata tttacaacaa ctatttcaat aaaatcatcg acagcggaat taattcgagg     780
atgggcgcgc gcatcagaat tgagaacaac ctctttgaaa acgccaaaga tccgattgtc     840
tcttggtaca gcagttcacc gggctattgg catgtatcca acaacaaatt tgtaaactct     900
agggcagta tgccgactac ctctactaca acctataatc cgccatacag ctactcactc     960
gacaatgtcg acaatgtaaa atcaatcgtc aagcaaaatg ccggagtcgg caaatcaat    1020
ccataa                                                              1026

<210> SEQ ID NO 4
<211> LENGTH: 341
<212> TYPE: PRT
<213> ORGANISM: Bacillus licheniformis  ATCC 14580

<400> SEQUENCE: 4

Met Lys Lys Leu Ile Ser Ile Ile Phe Ile Phe Val Leu Gly Val Val
1               5                   10                  15

Gly Ser Leu Thr Ala Ala Val Ser Ala Glu Ala Ala Ser Ala Leu Asn
                20                  25                  30

-continued

Ser Gly Lys Val Asn Pro Leu Ala Asp Phe Ser Leu Lys Gly Phe Ala
          35                  40                  45

Ala Leu Asn Gly Gly Thr Thr Gly Glu Gly Gln Thr Val Thr
 50                  55                  60

Val Thr Thr Gly Asp Gln Leu Ile Ala Ala Leu Lys Asn Lys Asn Ala
 65                  70                  75                  80

Asn Thr Pro Leu Lys Ile Tyr Val Asn Gly Thr Ile Thr Thr Ser Asn
                 85                  90                  95

Thr Ser Ala Ser Lys Ile Asp Val Lys Asp Val Ser Asn Val Ser Ile
             100                 105                 110

Val Gly Ser Gly Thr Lys Gly Glu Leu Lys Gly Ile Gly Ile Lys Ile
             115                 120                 125

Trp Arg Ala Asn Asn Ile Ile Ile Arg Asn Leu Lys Ile His Glu Val
130                 135                 140

Ala Ser Gly Asp Lys Asp Ala Ile Gly Ile Glu Gly Pro Ser Lys Asn
145                 150                 155                 160

Ile Trp Val Asp His Asn Glu Leu Tyr His Ser Leu Asn Val Asp Lys
                 165                 170                 175

Asp Tyr Tyr Asp Gly Leu Phe Asp Val Lys Arg Asp Ala Glu Tyr Ile
             180                 185                 190

Thr Phe Ser Trp Asn Tyr Val His Asp Gly Trp Lys Ser Met Leu Met
             195                 200                 205

Gly Ser Ser Asp Ser Asp Asn Tyr Asn Arg Thr Ile Thr Phe His His
210                 215                 220

Asn Trp Phe Glu Asn Leu Asn Ser Arg Val Pro Ser Phe Arg Phe Gly
225                 230                 235                 240

Glu Gly His Ile Tyr Asn Asn Tyr Phe Asn Lys Ile Ile Asp Ser Gly
                 245                 250                 255

Ile Asn Ser Arg Met Gly Ala Arg Ile Arg Ile Glu Asn Asn Leu Phe
             260                 265                 270

Glu Asn Ala Lys Asp Pro Ile Val Ser Trp Tyr Ser Ser Pro Gly
             275                 280                 285

Tyr Trp His Val Ser Asn Asn Lys Phe Val Asn Ser Arg Gly Ser Met
290                 295                 300

Pro Thr Thr Ser Thr Thr Thr Tyr Asn Pro Pro Tyr Ser Tyr Ser Leu
305                 310                 315                 320

Asp Asn Val Asp Asn Val Lys Ser Ile Val Lys Gln Asn Ala Gly Val
                 325                 330                 335

Gly Lys Ile Asn Pro
             340

<210> SEQ ID NO 5
<211> LENGTH: 1530
<212> TYPE: DNA
<213> ORGANISM: Bacillus sp.

<400> SEQUENCE: 5
atgatgaaga tgagaaaagc attaagtgta ttagtgattt tcggattatt cgtatctttt      60
tttagttttg gtcatcaagg agcagaagcg gcatcatttc agtctaataa aaattatcat     120
ctagtgaatg tgaacagtgg caagtactta gaagtggggg ctgcctcaac agagaacggt     180
gcaaatgtcc aacaatggga aaatacgaat tgtcattgtc aacaatggcg attggtgcaa     240
aatcaggatg gttattatga gattgtaaac cgacatagtg gcaaagcatt ggatgtattt     300
gaacgttctt cagctgatgg agcgaacatt gtacaatggg attcgaatgg acgtagcaat     360

```
caacaatgga cgattcaaca agtgggttcc tcttataaaa tagttagcag acatagtggg      420
aaggcactcg aagtatttaa ccattctaat caaaatggag caaatgtcgt acagtggcaa      480
gattttggta atccgaatca actttggaat atcgtcgagg ttggttcagg acaagctcac      540
gatttcagta agccgttggg gtatgcctca atgaatggcg ggaccactgg cggtcaaggt      600
ggacgagtcg aatacgcgag tactggctct caactacaaa aattaatcga tgatcgaagt      660
cgaagcaata atcccaatca accacttacc atttatgtaa ctgggaaaat caccctgcaa      720
aactcctctg atgataaaat tgaagtgaaa aatcatcgtg acaagctcca tgaaatacgt      780
aatctgtcta tcataggtca aggaacaaga ggagagtttg atggcattgg tttacgatta      840
attaatgcgc acaatgtcat tgtgcgtaat ctctccattc accatgtacg agctggttca      900
ggtgaaggta catcaattga agttactcaa ggaagtaaga atatttggat tgatcataac      960
gaattttata gtcaactgga tgggaataac aaccctgatc tgtatgatgg tcttgtcgat     1020
attaaacgga attcggagta cattacggtc tcttggaaca gtttgagaa tcattggaaa     1080 acgatgctcg tcggccatac cgataacgca tcattagcac ctgataaagt tacgtaccac     1140
cacaactttt tccacaatct taattccaga gttccgttaa ttcgattcgc agatgttcat     1200
atggttaaca actatttcaa agatattaaa gatacagcaa ttaatagtcg tatgggagca     1260
agagtatttg tagaaaataa ctattttgag aatgtaggat caggtcaaca agatccgacc     1320
acacgacaaa ttaaaactgc tgttgggtgg ttttatggta gttctagcac tggatattgg     1380
aatttaagag gaaatcaatt tattaacaca ccatcaagcc acttgtcttc cacaacgaat     1440
ttcacaccac cttatcagtt caacgcccaa tccgctcaag atgcaaagca agccgttgaa     1500
cagttttcgg gtgtaggggt tgtacagtag                                      1530
```

<210> SEQ ID NO 6
<211> LENGTH: 509
<212> TYPE: PRT
<213> ORGANISM: Bacillus sp.

<400> SEQUENCE: 6

```
Met Met Lys Met Arg Lys Ala Leu Ser Val Leu Val Ile Phe Gly Leu
 1               5                  10                  15

Phe Val Ser Phe Phe Ser Phe Gly His Gln Gly Ala Glu Ala Ala Ser
                20                  25                  30

Phe Gln Ser Asn Lys Asn Tyr His Leu Val Asn Val Asn Ser Gly Lys
            35                  40                  45

Tyr Leu Glu Val Gly Ala Ala Ser Thr Glu Asn Gly Ala Asn Val Gln
        50                  55                  60

Gln Trp Glu Asn Thr Asn Cys His Cys Gln Gln Trp Arg Leu Val Gln
65                  70                  75                  80

Asn Gln Asp Gly Tyr Tyr Glu Ile Val Asn Arg His Ser Gly Lys Ala
                85                  90                  95

Leu Asp Val Phe Glu Arg Ser Ala Asp Gly Ala Asn Ile Val Gln
            100                 105                 110

Trp Asp Ser Asn Gly Arg Ser Asn Gln Gln Trp Thr Ile Gln Gln Val
        115                 120                 125

Gly Ser Ser Tyr Lys Ile Val Ser Arg His Ser Gly Lys Ala Leu Glu
    130                 135                 140

Val Phe Asn His Ser Asn Gln Asn Gly Ala Asn Val Val Gln Trp Gln
145                 150                 155                 160
```

```
Asp Phe Gly Asn Pro Asn Gln Leu Trp Asn Ile Val Glu Val Gly Ser
                165                 170                 175
Gly Gln Ala His Asp Phe Ser Lys Pro Leu Gly Tyr Ala Ser Met Asn
            180                 185                 190
Gly Gly Thr Gly Gly Gln Gly Gly Arg Val Glu Tyr Ala Ser Thr
        195                 200                 205
Gly Ser Gln Leu Gln Lys Leu Ile Asp Asp Arg Ser Arg Ser Asn Asn
    210                 215                 220
Pro Asn Gln Pro Leu Thr Ile Tyr Val Thr Gly Lys Ile Thr Leu Gln
225                 230                 235                 240
Asn Ser Ser Asp Asp Lys Ile Glu Val Lys Asn His Arg Gly Gln Ala
                245                 250                 255
His Glu Ile Arg Asn Leu Ser Ile Ile Gly Gln Gly Thr Arg Gly Glu
            260                 265                 270
Phe Asp Gly Ile Gly Leu Arg Leu Ile Asn Ala His Asn Val Ile Val
        275                 280                 285
Arg Asn Leu Ser Ile His His Val Arg Ala Gly Ser Gly Glu Gly Thr
    290                 295                 300
Ser Ile Glu Val Thr Gln Gly Ser Lys Asn Ile Trp Ile Asp His Asn
305                 310                 315                 320
Glu Phe Tyr Ser Gln Leu Asp Gly Asn Asn Asn Pro Asp Leu Tyr Asp
                325                 330                 335
Gly Leu Val Asp Ile Lys Arg Asn Ser Glu Tyr Ile Thr Val Ser Trp
            340                 345                 350
Asn Lys Phe Glu Asn His Trp Lys Thr Met Leu Val Gly His Thr Asp
        355                 360                 365
Asn Ala Ser Leu Ala Pro Asp Lys Val Thr Tyr His His Asn Phe Phe
    370                 375                 380
His Asn Leu Asn Ser Arg Val Pro Leu Ile Arg Phe Ala Asp Val His
385                 390                 395                 400
Met Val Asn Asn Tyr Phe Lys Asp Ile Lys Asp Thr Ala Ile Asn Ser
                405                 410                 415
Arg Met Gly Ala Arg Val Phe Val Glu Asn Asn Tyr Phe Glu Asn Val
            420                 425                 430
Gly Ser Gly Gln Gln Asp Pro Thr Thr Arg Gln Ile Lys Thr Ala Val
        435                 440                 445
Gly Trp Phe Tyr Gly Ser Ser Thr Gly Tyr Trp Asn Leu Arg Gly
    450                 455                 460
Asn Gln Phe Ile Asn Thr Pro Ser Ser His Leu Ser Ser Thr Asn
465                 470                 475                 480
Phe Thr Pro Pro Tyr Gln Phe Asn Ala Gln Ser Ala Gln Asp Ala Lys
                485                 490                 495
Gln Ala Val Glu Gln Phe Ser Gly Val Gly Val Val Gln
            500                 505

<210> SEQ ID NO 7
<211> LENGTH: 1047
<212> TYPE: DNA
<213> ORGANISM: Bacillus sp.

<400> SEQUENCE: 7
atggacaaac tttatattga aaaaggaagt gagagtatga tgagatcaag catcgtcaaa      60
ctagttgctt tcagtattgt gtttatgtta tggctcggtg tatcctttca aacggcagaa     120
gcgaatacgc caaatttcaa cttacaaggc tttgccacgt taaatggggg aacaactggt     180
```

```
ggcgctggtg gagatgtagt gacggttcgt acagggaatg agttaataaa cgctttgaag    240
tccaaaaacc ctaatcggcc gttaacaatt tatgttaacg gtacgataac gcctaataat    300
acgtctgata gtaagatcga cattaaggat gtttccaatg tatcgatttt aggggttggc    360
acaaatggcc gattaaacgg gatcggtatt aaagtatggc gagcgaataa tatcattatt    420
cgaaacttga caatccatga agtccataca ggtgataaaa atgcgattag catgattagc    480
attgaaggac catctcgaaa catttgggtt gaccataacg agctttatgc cagcttgaat    540
gttcataaag atcactatga cggcttgttt gacgtaaagc gcgatgctta caatattacc    600
ttctcttgga attatgtcca tgatggctgg aaagcgatgc tcatgggaa ttccgatagt    660 gataattatg accgaaacat aacattccac cataactact tcaaaaactt aaactctcgt    720
gtacctgcgt accgttttgg aaaggcgcac ttgtttagca attactttga gaacatttta    780
gaaacaggca tcaattcacg gatgggagcg gaaatgctcg ttgaacataa cgttttgag    840 aatgccacca acccgctagg attctggcat agcagtcgaa caggttattg gaatgtagcc    900
aataaccgct atatcaatag cacgggcagc atgccgacca cttccacgac caattatcga    960
cctccttacc cctatacggg cacacctgtt ggtgatgtga atcagttgt cacacgttat   1020 gcgggagttg gtgtcatcca accgtaa                                      1047
```

<210> SEQ ID NO 8
<211> LENGTH: 348
<212> TYPE: PRT
<213> ORGANISM: Bacillus sp.

<400> SEQUENCE: 8

Met Asp Lys Leu Tyr Ile Glu Lys Gly Ser Glu Ser Met Met Arg Ser
1               5                   10                  15

Ser Ile Val Lys Leu Val Ala Phe Ser Ile Val Phe Met Leu Trp Leu
            20                  25                  30

Gly Val Ser Phe Gln Thr Ala Glu Ala Asn Thr Pro Asn Phe Asn Leu
        35                  40                  45

Gln Gly Phe Ala Thr Leu Asn Gly Gly Thr Gly Gly Ala Gly Gly
    50                  55                  60

Asp Val Val Thr Val Arg Thr Gly Asn Glu Leu Ile Asn Ala Leu Lys
65                  70                  75                  80

Ser Lys Asn Pro Asn Arg Pro Leu Thr Ile Tyr Val Asn Gly Thr Ile
                85                  90                  95

Thr Pro Asn Asn Thr Ser Asp Ser Lys Ile Asp Ile Lys Asp Val Ser
            100                 105                 110

Asn Val Ser Ile Leu Gly Val Gly Thr Asn Gly Arg Leu Asn Gly Ile
        115                 120                 125

Gly Ile Lys Val Trp Arg Ala Asn Asn Ile Ile Arg Asn Leu Thr
    130                 135                 140

Ile His Glu Val His Thr Gly Asp Lys Asp Ala Ile Ser Met Ile Ser
145                 150                 155                 160

Ile Glu Gly Pro Ser Arg Asn Ile Trp Val Asp His Asn Glu Leu Tyr
                165                 170                 175

Ala Ser Leu Asn Val His Lys Asp His Tyr Asp Gly Leu Phe Asp Val
            180                 185                 190

Lys Arg Asp Ala Tyr Asn Ile Thr Phe Ser Trp Asn Tyr Val His Asp
        195                 200                 205

Gly Trp Lys Ala Met Leu Met Gly Asn Ser Asp Ser Asp Asn Tyr Asp

```
                210                 215                 220
Arg Asn Ile Thr Phe His His Asn Tyr Phe Lys Asn Leu Asn Ser Arg
225                 230                 235                 240

Val Pro Ala Tyr Arg Phe Gly Lys Ala His Leu Phe Ser Asn Tyr Phe
                245                 250                 255

Glu Asn Ile Leu Glu Thr Gly Ile Asn Ser Arg Met Gly Ala Glu Met
                260                 265                 270

Leu Val Glu His Asn Val Phe Glu Asn Ala Thr Asn Pro Leu Gly Phe
            275                 280                 285

Trp His Ser Ser Arg Thr Gly Tyr Trp Asn Val Ala Asn Asn Arg Tyr
            290                 295                 300

Ile Asn Ser Thr Gly Ser Met Pro Thr Thr Ser Thr Thr Asn Tyr Arg
305                 310                 315                 320

Pro Pro Tyr Pro Tyr Thr Val Thr Pro Val Gly Asp Val Lys Ser Val
                325                 330                 335

Val Thr Arg Tyr Ala Gly Val Gly Val Ile Gln Pro
                340                 345
```

<210> SEQ ID NO 9
<211> LENGTH: 1008
<212> TYPE: DNA
<213> ORGANISM: Bacillus sp.

<400> SEQUENCE: 9

```
atgagaaaac tcttatcgat gatgactgcg cttgtactca tgtttggaat catggttgta      60
ccttctatag ccaaaggtga aagcgattcc actatgaatg ctgattttc catgcaaggt     120
tttgcgacac ttaatggcgg aaccacagga ggagccggcg gcaaaccgt aaccgtttct     180
accggagacg aactgctggc ggccttgaag aacaaaaaca gcaatacacc cctgacgatt     240
tatgtaaacg gtaccataac gccatcaaat acgtccgcaa gcaaaattga tattaaagac     300
gtaaacgatg tttcgatctt aggtgttggc actcaaggcg aatttaacgg cattggcatt     360
aaagtatggc gagccaataa cattattctc cgcaacttga aaatacatca cgtcaataca     420
ggcgacaaag atgccattag cattgaagga ccatccaaaa acatatgggt tgaccacaat     480
gagctctaca atagtcttga tgtccataag gattactacg atggtctttt tgatgtcaaa     540
cgggacgcgg attacattac attctcgtgg aattatgttc atgatagctg aagagcatg     600
ctgatgggat cttctgattc cgattcgtac aaccgaaaaa tcacattcca caataactac     660
tttgaaaacc tcaattcacg tgtaccttcc atacgctttg gcgaagccca catcttcagc     720
aactactaca atggcattaa tgaaaccggc atcaactccc gcatggggc aaaagtgcgc     780
atcgaggaaa atctatttga acgcgcaaac aacccgatcg tcagtcgcga cagtcgccaa     840
gtcgggtatt ggcacttgat aaacaatcac tttactcaat caacgggcga aattccaacg     900
acttcaacaa tcacatataa cccaccttat tcctatcaag ctactccggt tggccaagta     960
aaagatgtgg tcgtgcgaa tgctggtgtt ggcaaagtaa caccttaa               1008
```

<210> SEQ ID NO 10
<211> LENGTH: 335
<212> TYPE: PRT
<213> ORGANISM: Bacillus sp.

<400> SEQUENCE: 10

```
Met Arg Lys Leu Leu Ser Met Met Thr Ala Leu Val Leu Met Phe Gly
1               5                   10                  15
```

```
Ile Met Val Val Pro Ser Ile Ala Lys Gly Glu Ser Asp Ser Thr Met
             20                  25                  30

Asn Ala Asp Phe Ser Met Gln Gly Phe Ala Thr Leu Asn Gly Gly Thr
         35                  40                  45

Thr Gly Gly Ala Gly Gly Gln Thr Val Thr Val Ser Thr Gly Asp Glu
 50                  55                  60

Leu Leu Ala Ala Leu Lys Asn Lys Asn Ser Asn Thr Pro Leu Thr Ile
 65                  70                  75                  80

Tyr Val Asn Gly Thr Ile Thr Pro Ser Asn Thr Ser Ala Ser Lys Ile
                 85                  90                  95

Asp Ile Lys Asp Val Asn Asp Val Ser Ile Leu Gly Val Gly Thr Gln
            100                 105                 110

Gly Glu Phe Asn Gly Ile Gly Ile Lys Val Trp Arg Ala Asn Asn Ile
        115                 120                 125

Ile Leu Arg Asn Leu Lys Ile His His Val Asn Thr Gly Asp Lys Asp
130                 135                 140

Ala Ile Ser Ile Glu Gly Pro Ser Lys Asn Ile Trp Val Asp His Asn
145                 150                 155                 160

Glu Leu Tyr Asn Ser Leu Asp Val His Lys Asp Tyr Tyr Asp Gly Leu
                165                 170                 175

Phe Asp Val Lys Arg Asp Ala Asp Tyr Ile Thr Phe Ser Trp Asn Tyr
            180                 185                 190

Val His Asp Ser Trp Lys Ser Met Leu Met Gly Ser Ser Asp Ser Asp
        195                 200                 205

Ser Tyr Asn Arg Lys Ile Thr Phe His Asn Asn Tyr Phe Glu Asn Leu
210                 215                 220

Asn Ser Arg Val Pro Ser Ile Arg Phe Gly Glu Ala His Ile Phe Ser
225                 230                 235                 240

Asn Tyr Tyr Asn Gly Ile Asn Glu Thr Gly Ile Asn Ser Arg Met Gly
                245                 250                 255

Ala Lys Val Arg Ile Glu Glu Asn Leu Phe Glu Arg Ala Asn Asn Pro
            260                 265                 270

Ile Val Ser Arg Asp Ser Arg Gln Val Gly Tyr Trp His Leu Ile Asn
        275                 280                 285

Asn His Phe Thr Gln Ser Thr Gly Glu Ile Pro Thr Thr Ser Thr Ile
290                 295                 300

Thr Tyr Asn Pro Pro Tyr Ser Tyr Gln Ala Thr Pro Val Gly Gln Val
305                 310                 315                 320

Lys Asp Val Val Arg Ala Asn Ala Gly Val Gly Lys Val Thr Gly
                325                 330                 335
```

<210> SEQ ID NO 11
<211> LENGTH: 1482
<212> TYPE: DNA
<213> ORGANISM: Clostridium thermocellum

<400> SEQUENCE: 11

| | | | | | |
|---|---|---|---|---|---|
| gcttctgcct | taaactcggg | caaagtaaat | ccgcttgccg | acttcagctt | aaaaggcttt | 60 |
| gccgcactaa | acggcggaac | aacgggcgga | gaaggcggtc | agacggtaac | cgtaacaacg | 120 |
| ggagatcagc | tgattgcggc | attaaaaaat | aagaatgcaa | atacgccttt | aaaaatttat | 180 |
| gtcaacggca | ccattacaac | atcaaataca | tccgcatcaa | agattgacgt | caaagacgtg | 240 |
| tcaaacgtat | cgattgtcgg | atcagggacc | aaagggggaac | tcaaagggat | cggcatcaaa | 300 |
| atatggcggg | ccaacaacat | catcatccgc | aacttgaaaa | ttcacgaggt | cgcctcaggc | 360 |

```
gataaagacg cgatcggcat tgaaggccct tctaaaaaca tttgggttga tcataatgag    420
ctttaccaca gcctgaacgt tgacaaagat tactatgacg gattatttga cgtcaaaaga    480
gatgcggaat atattacatt ctcttggaac tatgtgcacg atggatggaa tcaatgctg     540 atgggttcat cggacagcga taattacaac aggacgatta cattccatca taactggttt    600
gagaatctga attcgcgtgt gccgtcattc cgtttcggag aaggccatat ttacaacaac    660
tatttcaata aaatcatcga cagcggaatt aattcgagga tgggcgcgcg catcagaatt    720
gagaacaacc tctttgaaaa cgccaaagat ccgattgtct cttggtacag cagttcaccg    780
ggctattggc atgtatccaa caacaaattt gtaaactcta ggggcagtat gccgactacc    840
tctactacaa cctataatcc gccatacagc tactcactcg acaatgtcga caatgtaaaa    900
tcaatcgtca agcaaaatgc cggagtcggc aaaatccagc gcagaccgcc aacaccgacc    960
ccgacttcac cgccaagcgc aaatacaccg gtatcaggca atttgaaggt tgaattctac   1020
aacagcaatc cttcagatac tactaactca atcaatcctc agttcaaggt tactaatacc   1080
ggaagcagtg caattgattt gtccaaactc acattgagat attattatac agtagacgga   1140
cagaaagatc agaccttctg gtgtgaccat gctgcaataa tcggcagtaa cggcagctac   1200
aacggaatta cttcaaatgt aaaaggaaca tttgtaaaaa tgagttcctc aacaaataac   1260
gcagacacct accttgaaat aagctttaca ggcggaactc ttgaaccggg tgcacatgtt   1320
cagatacaag gtagatttgc aaagaatgac tggagtaact atacacagtc aaatgactac   1380
tcattcaagt ctcgttcaca gtttgttgaa tgggatcagg taacagcata cttgaacggt   1440
gttcttgtat ggggtaaaga acccggtggc agtgtagtat ag                      1482
```

<210> SEQ ID NO 12
<211> LENGTH: 493
<212> TYPE: PRT
<213> ORGANISM: Clostridium thermocellum

<400> SEQUENCE: 12

```
Ala Ser Ala Leu Asn Ser Gly Lys Val Asn Pro Leu Ala Asp Phe Ser
 1               5                  10                  15

Leu Lys Gly Phe Ala Ala Leu Asn Gly Gly Thr Thr Gly Gly Glu Gly
            20                  25                  30

Gly Gln Thr Val Thr Val Thr Thr Gly Asp Gln Leu Ile Ala Ala Leu
        35                  40                  45

Lys Asn Lys Asn Ala Asn Thr Pro Leu Lys Ile Tyr Val Asn Gly Thr
    50                  55                  60

Ile Thr Thr Ser Asn Thr Ser Ala Ser Lys Ile Asp Val Lys Asp Val
65                  70                  75                  80

Ser Asn Val Ser Ile Val Gly Ser Gly Thr Lys Gly Glu Leu Lys Gly
                85                  90                  95

Ile Gly Ile Lys Ile Trp Arg Ala Asn Asn Ile Ile Arg Asn Leu
            100                 105                 110

Lys Ile His Glu Val Ala Ser Gly Asp Lys Asp Ala Ile Gly Ile Glu
        115                 120                 125

Gly Pro Ser Lys Asn Ile Trp Val Asp His Asn Glu Leu Tyr His Ser
    130                 135                 140

Leu Asn Val Asp Lys Asp Tyr Tyr Asp Gly Leu Phe Asp Val Lys Arg
145                 150                 155                 160

Asp Ala Glu Tyr Ile Thr Phe Ser Trp Asn Tyr Val His Asp Gly Trp
                165                 170                 175
```

-continued

```
Lys Ser Met Leu Met Gly Ser Ser Asp Ser Asp Asn Tyr Asn Arg Thr
            180                 185                 190
Ile Thr Phe His His Asn Trp Phe Glu Asn Leu Asn Ser Arg Val Pro
        195                 200                 205
Ser Phe Arg Phe Gly Glu Gly His Ile Tyr Asn Asn Tyr Phe Asn Lys
        210                 215                 220
Ile Ile Asp Ser Gly Ile Asn Ser Arg Met Gly Ala Arg Ile Arg Ile
225                 230                 235                 240
Glu Asn Asn Leu Phe Glu Asn Ala Lys Asp Pro Ile Val Ser Trp Tyr
            245                 250                 255
Ser Ser Ser Pro Gly Tyr Trp His Val Ser Asn Asn Lys Phe Val Asn
            260                 265                 270
Ser Arg Gly Ser Met Pro Thr Thr Ser Thr Thr Thr Tyr Asn Pro Pro
            275                 280                 285
Tyr Ser Tyr Ser Leu Asp Asn Val Asp Asn Val Lys Ser Ile Val Lys
            290                 295                 300
Gln Asn Ala Gly Val Gly Lys Ile Gln Arg Arg Pro Thr Pro Thr
305                 310                 315                 320
Pro Thr Ser Pro Pro Ser Ala Asn Thr Pro Val Ser Gly Asn Leu Lys
                325                 330                 335
Val Glu Phe Tyr Asn Ser Asn Pro Ser Asp Thr Thr Asn Ser Ile Asn
                340                 345                 350
Pro Gln Phe Lys Val Thr Asn Thr Gly Ser Ser Ala Ile Asp Leu Ser
            355                 360                 365
Lys Leu Thr Leu Arg Tyr Tyr Tyr Thr Val Asp Gly Gln Lys Asp Gln
    370                 375                 380
Thr Phe Trp Cys Asp His Ala Ala Ile Ile Gly Ser Asn Gly Ser Tyr
385                 390                 395                 400
Asn Gly Ile Thr Ser Asn Val Lys Gly Thr Phe Val Lys Met Ser Ser
                405                 410                 415
Ser Thr Asn Asn Ala Asp Thr Tyr Leu Glu Ile Ser Phe Thr Gly Gly
                420                 425                 430
Thr Leu Glu Pro Gly Ala His Val Gln Ile Gln Gly Arg Phe Ala Lys
            435                 440                 445
Asn Asp Trp Ser Asn Tyr Thr Gln Ser Asn Asp Tyr Ser Phe Lys Ser
    450                 455                 460
Arg Ser Gln Phe Val Glu Trp Asp Gln Val Thr Ala Tyr Leu Asn Gly
465                 470                 475                 480
Val Leu Val Trp Gly Lys Glu Pro Gly Gly Ser Val Val
            485                 490
```

<210> SEQ ID NO 13
<211> LENGTH: 1506
<212> TYPE: RNA
<213> ORGANISM: Bacillus sp. I534

<400> SEQUENCE: 13

```
gacgaacgcu ggcggcgugc cuaauacaug caagucgagc ggauugaagg gagcuugcuc      60
ccggauauua gcgcggacg ggugaguaac acgugggcaa ccugcccuuu agacugggau     120
aacuccggga aaccggugcu aauaccggau aacacuuuga accuccuggu ucgaaguuga     180
aagauggccu ucgugcuauc acuaaaggau gggcccgcgg cgcauuagcu aguugguaag     240
guaauggcuu accaaggcaa cgaugcguag ccgaccugag aggugaucg gccacacugg     300
```

-continued

```
gacugagaca cggcccagac uccuacggga ggcagcagua gggaaucuuc cgcaauggac    360
gaaagucuga cggagcaacg ccgcgugagu gaggaaggcc uucggucgu aaagcucugu     420 ugugagggaa gaacaaguau cgguugaaua agccgguacc uugacgguac cucaccagaa    480
agccacggcu aacuacgugc cagcagccgc gguaauacgu agguggcaag cguguccgg     540 aauuauuggg cguaaagcgc gcgcaggcgg cuucuuaagu cugaugugaa aucucggggc    600
ucaaccccga gcggccauug gaaacugggg agcuugagug cagaagagga gaguggaauu    660
ccacguguag cggugaaaug cguagauaug uggaggaaca ccaguggcga aggcgacucu    720
cuggucugua acugacgcug aggcgcgaaa gcgugggag caaacaggau uagauacccu     780
gguaguccac gccguaaacg augagugcua ggguuuaggg guuucgaugc ccguagugcc    840
gaaguaaaca cauuaagcac uccgccuggg gaguacgacc gcaagguuga aacucaaagg    900
aauugacggg gacccgcaca agcaguggag caugugguuu aauucgaagc aacgcgaaga    960
accuuaccag gucuugacau ccuuugacca cucuggagac agagcuuccc cuucggggc    1020 aaagugacag gugugcaug guugucguca gcucgugucg ugagauguug gguuaagucc    1080
cgcaacgagc gcaacccuug aucuuaguug ccagcauuua guugggcacu cuaaggugac    1140
ugccggugac aaaccggagg aaggugggga cgacgucaaa ucaucaugcc ccuuaugacc    1200
ugggcuacac acgugcuaca auggauggua caaagggguug cgaagccgcg aggugaagcc    1260
aaucccauaa agccauucuc aguucggauu gcaggcugca acucgccugc augaagccgg    1320
aauugcuagu aaucgcggau cagcaugccg cggugaauac guucccgggu cuguacaca    1380 ccgcccguca caccacgaga guuuguaaca cccgaagucg gugagguaac cuuuuggagc    1440
cagccgccua aggugggaca aaugauuggg gugaagucgu aacaagguag ccguaucgga    1500
aggugc                                                              1506
```

<210> SEQ ID NO 14
<211> LENGTH: 1508
<212> TYPE: RNA
<213> ORGANISM: Bacillus sp.

<400> SEQUENCE: 14

```
gacgaacgcu ggcggcgugc cuaauacaug caagucgagc ggacauuuag gagcuugcuc     60
cuaaauguua gcggcggacg ggugaguaac acgugggcaa ccugcccugu agacugggau    120
aacaucgaga aaucgugcu aauaccggau aaucuugagg auugcauaau ccucuuguaa     180
aagauggcuc cggcuaucac uacgggaugg gcccgcggcg cauuagcuag uugguaaggu    240
aacggcuuac caaggcgacg augcguagcc gaccugagag ggugaucggc cacacuggga    300
cugagacacg gcccagacuc cuacggggagg cagcaguagg gaaucuuccg caauggacga    360
aagucugacg gagcaacgcc gcgugaguga ugaagggguu cggcucguaa agcucuguug    420
uuagggaaga caagugccg uucaaauagg gcggaccuu gacgguaccu aaccagaaag     480
ccacggcuaa cuacgugcca gcagccgcgu aauacguagg ugcaagcg uguccggaa      540 uuauuggcg uaaagcgcgc gcaggcgguc uuuuaagucu gaugugaaau cucggggcuc    600
aaccccgagc ggucauugga acugggagaa cuugaguaca agaggagag ggaauucc       660 acguguagcg gugaaaugcg uagauaugug gaggaacacc aguggcgaag cgacucucu    720 ggucuguaac ugacgcugag gcgcgaaagc gugggagca acaggauua gauacccugg    780 uaguccacgc cguaaacgau gagugcuagg guuaggggu uucgaugccc uuagugccga    840
aguuaacaca uuaagcacuc cgccugggga guacgaccgc aagguugaaa cucaaaggaa    900
```

-continued

```
uugacggggg cccgcacaag caguggagca ugugguuuaa uucgaagcaa cgcgaagaac      960
cuuaccaggu cuugacaucc uuaugaccuc ccuagagaua gggauuuccc uucggggaca     1020
uaagugacag guggugcaug guugucguca gcucgugucg ugagauguug gguuaaguco     1080 cgcaacgagc gcaacccuug aucuuaguug ccagcauuua guugggcacu cuaaggugac     1140
ugccggugau aaaccggagg aaggugggga ugacgucaaa ucaucaugcc ccuuaugacc     1200
ugggcuacac acgugcuaca auggauggua caaagagcag caaaaccgcg aggucgagcc     1260
aaucucauaa agccauucuc aguucggauu guaggcugca acucgccuac augaagccgg     1320
aauugcuagu aaucgcggau cagcaugccg cggugaauac guucccgggc cuuguacaca     1380
ccgcccguca caccacgaga guuuguaaca cccgaagucg guggaguaac ccuuacggga     1440
gcuagccgcc uagguuggga cagaugauug gggugaaguc guaacaaggu agccguaucg     1500
gaaggugc                                                              1508

<210> SEQ ID NO 15
<211> LENGTH: 42
<212> TYPE: DNA
<213> ORGANISM: Artificial Sequence
<220> FEATURE:
<223> OTHER INFORMATION: Primer

<400> SEQUENCE: 15
gtcgccgggg cggccgctat caattggtaa ctgtatctca gc                          42

<210> SEQ ID NO 16
<211> LENGTH: 64
<212> TYPE: DNA
<213> ORGANISM: Artificial Sequence
<220> FEATURE:
<223> OTHER INFORMATION: Primer

<400> SEQUENCE: 16
gtcgcccggg agctctgatc aggtaccaag cttgtcgacc tgcagaatga ggcagcaaga      60
agat                                                                  64

<210> SEQ ID NO 17
<211> LENGTH: 61
<212> TYPE: DNA
<213> ORGANISM: Artificial Sequence
<220> FEATURE:
<223> OTHER INFORMATION: Primer

<400> SEQUENCE: 17
gtcggcggcc gctgatcacg taccaagctt gtcgacctgc agaatgaggc agcaagaaga      60
t                                                                     61

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
gtcggagctc tatcaattgg taactgtatc tcagc                                 35

<210> SEQ ID NO 19
<211> LENGTH: 35
<212> TYPE: DNA
```

```
<213> ORGANISM: Artificial Sequence
<220> FEATURE:
<223> OTHER INFORMATION: Primer

<400> SEQUENCE: 19
aacagctgat cacgactgat cttttagctt ggcac                              35

<210> SEQ ID NO 20
<211> LENGTH: 37
<212> TYPE: DNA
<213> ORGANISM: Artificial Sequence
<220> FEATURE:
<223> OTHER INFORMATION: Primer

<400> SEQUENCE: 20
aactgcagcc gcggcacatc ataatgggac aaatggg                            37

<210> SEQ ID NO 21
<211> LENGTH: 37
<212> TYPE: DNA
<213> ORGANISM: Artificial Sequence
<220> FEATURE:
<223> OTHER INFORMATION: Primer

<400> SEQUENCE: 21
ctgcagccgc ggcagctgct tcaaatcagc caacttc                            37

<210> SEQ ID NO 22
<211> LENGTH: 43
<212> TYPE: DNA
<213> ORGANISM: Artificial Sequence
<220> FEATURE:
<223> OTHER INFORMATION: Primer

<400> SEQUENCE: 22
gcgttgagac gcgcggccgc tttactctgc acacaggcag agc                     43

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
ctaactgcag ccgcggcagc ttctgcctta aactcgggc                          39

<210> SEQ ID NO 24
<211> LENGTH: 42
<212> TYPE: DNA
<213> ORGANISM: Artificial Sequence
<220> FEATURE:
<223> OTHER INFORMATION: Primer

<400> SEQUENCE: 24
gcgttgagac gcgcggccgc tgaatgcccc ggacgtttca cc                      42

<210> SEQ ID NO 25
<211> LENGTH: 43
<212> TYPE: DNA
<213> ORGANISM: Artificial Sequence
<220> FEATURE:
<223> OTHER INFORMATION: Primer

<400> SEQUENCE: 25
cattctgcag ccgcggcaaa tacgccaaat ttcaacttac aag                     43
```

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26
cagcagtagc ggccgcttac ggttggatga caccaactc      39

<210> SEQ ID NO 27
<211> LENGTH: 39
<212> TYPE: DNA
<213> ORGANISM: Artificial Sequence
<220> FEATURE:
<223> OTHER INFORMATION: Primer

<400> SEQUENCE: 27
cctgcagccg cggcaaaagg tgaaagcgat tccactatg      39

<210> SEQ ID NO 28
<211> LENGTH: 39
<212> TYPE: DNA
<213> ORGANISM: Artificial Sequence
<220> FEATURE:
<223> OTHER INFORMATION: Primer

<400> SEQUENCE: 28
gttgagaaaa gcggccgcaa cggacactcg gctttagag      39

<210> SEQ ID NO 29
<211> LENGTH: 46
<212> TYPE: DNA
<213> ORGANISM: Artificial Sequence
<220> FEATURE:
<223> OTHER INFORMATION: Primer

<400> SEQUENCE: 29
cattctgcag ccgcggcagc atcatttcag tctaataaaa attatc      46

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
gacgacgtac aagcggccgc gctactgtac aacccctaca cc      42

<210> SEQ ID NO 31
<211> LENGTH: 127
<212> TYPE: DNA
<213> ORGANISM: Artificial Sequence
<220> FEATURE:
<223> OTHER INFORMATION: Primer

<400> SEQUENCE: 31
cgacaatgtc gacaatgtaa aatcaatcgt caagcaaaat gccggagtcg gcaaatcca      60 gcgcagaccg ccaacaccga ccccgacttc accgccaagc gcaaatacac cggtatcagg      120
caatttg      127

<210> SEQ ID NO 32

-continued

```
<211> LENGTH: 48
<212> TYPE: DNA
<213> ORGANISM: Artificial Sequence
<220> FEATURE:
<223> OTHER INFORMATION: Primer

<400> SEQUENCE: 32
gcgttgagac gcgcggccgc tataccacac tgccaccggg ttctttac         48
```

PECTATE LYASES

CROSS-REFERENCE TO RELATED APPLICATIONS

This application is a continuation of U.S. application Ser. No. 09/694,531 filed Oct. 23, 2000, now U.S. Pat. No. 6,368,843 which is a continuation of application Ser. No. 09/198,955 filed Nov. 24, 1998, now U.S. Pat. No. 6,187,580, which is a continuation-in-part of application Ser. Nos. 09/073,684, now U.S. Pat. No. 6,124,127, and Ser. No. 09/184,217, filed May 6, 1998 and Nov. 2, 1998, respectively now U.S. Pat. No. 6,258,590, and claims, under 35 U.S.C. 119, priority or the benefit of Danish application nos. 1343/97 and 1344/97, each filed Nov. 24, 1997, and of U.S. provisional application Nos. 60/067,240 and 60/067,249, each filed Dec. 2, 1997, the contents of which are fully incorporated herein by reference.

BACKGROUND OF THE INVENTION

1. Field of the Invention

The present invention relates to microbial pectate lyases, more specifically to microbial enzymes exhibiting pectate lyase activity as their major enzymatic activity in the neutral and alkaline pH ranges; to a method of producing such enzymes; and to methods for using such enzymes in the textile, detergent and cellulose fiber processing industries.

2. Description of Related Art

Pectin polymers are important constituents of plant cell walls. Pectin is a hetero-polysaccharide with a backbone composed of alternating homogalacturonan (smooth regions) and rhamnogalacturonan (hairy regions). The smooth regions are linear polymers of 1,4-linked alpha-D-galacturonic acid. The galacturonic acid residues can be methyl-esterified on the carboxyl group to a varying degree, usually in a non-random fashion with blocks of polygalacturonic acid being completely methyl-esterified.

Pectinases can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as pectate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and exo-poly-alpha-galacturonosidase (EC 3.2.1.82).

Pectate lyases have been cloned from different bacterial genera such as Erwinia, Pseudomonas, Klebsiella and Xanthomonas. Also from *Bacillus subtilis* (Nasser et al. (1993) FEBS 335:319–326) and Bacillus sp. YA-14 (Kim et al. (1994) Biosci. Biotech. Biochem. 58:947–949) cloning of a pectate lyase has been described. Purification of pectate lyases with maximum activity in the pH range of 8–10 produced by *Bacillus pumilus* (Dave and Vaughn (1971) J. Bacteriol. 108:166–174), *B. polymyxa* (Nagel and Vaughn (1961) Arch. Biochem. Biophys. 93:344–352), *B. stearothermophilus* (Karbassi and Vaughn (1980) Can. J. Microbiol. 26:377–384), Bacillus sp. (Hasegawa and Nagel (1966) J. Food Sci. 31:838–845) and Bacillus sp. RK9 (Kelly and Fogarty (1978) Can. J. Microbiol. 24:1164–1172) has been reported, however, no publication was found on cloning of pectate lyase encoding genes from these organisms. All the pectate lyases described require divalent cations for maximum activity, calcium ions being the most stimulatory.

WO 98/45393 discloses detergent compositions containing protopectinase with remarkable detergency agains muddy soilings.

Generally, pectinase producing microorganisms exhibit a broad range of pectin degrading or modifying enzymes. Often the microorganisms also produce cellulases and/or hemicellulases and complex multi-component enzyme preparations from such microorganisms may be difficult to optimize for various applications, they even may contain enzymes with detrimental effect. Thus, it is an object of the present invention to provide a pectin degrading enzyme exhibiting only the desired effects e.g. in detergents or different industrial processes.

SUMMARY OF THE INVENTION

The inventors have now found and identified several novel enzymes having substantial pectate lyase activity which perform excellent in various industrial process under neutral or alkaline conditions and have succeeded in identifying DNA sequences encoding such enzymes, these enzymes forming a novel class of pectate lyases having at least conserved region with identical partial amino acid sequence.

Accordingly, in a first aspect this invention relates to a pectate lyase comprising a first amino acid sequence consisting of seven (7) amino acid residues having the following sequence: Asn Leu Asn Ser Arg Val Pro (NLNSRVP) (SEQ ID NO: 2). In further embodiments, the pectate lyase may additionally hold a second amino acid sequence consisting of six (6) amino acid residues selected from the group consisting of the sequences Trp Val Asp His Asn Glu (WVDHNE) (SEQ ID NO: 4) and Trp Ile Asp His Asn Glu (WIDHNE) (SEQ ID NO: 2); and optionally also a third amino acid sequence consisting of three (3) amino acid residues having the following sequence: Ser Trp Asn (SWN).

The DNA sequences of five pectate lyases of the invention are listed in the sequence listing as SEQ ID NOS: 1, 3, 5, 7 and 9, respectively, and the deduced amino acid sequences are listed in the sequence listing as SEQ ID NOS: 2, 4, 6, 8 and 10, respectively. It is believed that the novel enzyme will be classified according to the Enzyme Nomenclature in the Enzyme Class EC 4.2.2.2. However, it should be noted that the enzyme of the invention also exhibits catalytic activity on pectin (which may be esterified) besides the activity on pectate and polygalacturonides conventionally attributed to enzymes belonging to EC 4.2.2.2.

In a second aspect, the present invention relates to a pectate lyase which is i) a polypeptide produced by *Bacillus agaradhaerens*, NCIMB 40482 or DSM 8721, or ii) a polypeptide comprising an amino acid sequence as shown in positions 27–359 of SEQ ID NO: 2, or iii) an analogue of the polypeptide defined in i) or ii) which is at least 45% homologous with said polypeptide, or iv) is derived from said polypeptide by substitution, deletion or addition of one or several amino acids, provided that the arginine in position 240, and optionally also the arginine in position 245, is conserved and the derived polypeptide is at least 42% homologous with said polypeptide, or v) is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having pectate lyase activity and comprising a sequence of nucleotides as shown in SEQ ID NO: 1 from nucleotide 79 to nucleotide 1077; (b) species homologs of (a); (c) polynucleotide molecules that encode a polypeptide having pectate lyase activity that is at least 45% identical to the amino acid sequence of SEQ ID NO: 2 from amino acid residue 27 to amino acid residue 359; (d) molecules complementary to (a), (b) or (c); and (e) degenerate nucleotide sequences of (a), (b), (c) or (d).

The plasmid pSJ1678 comprising the polynucleotide molecule (the DNA sequence) encoding a pectate lyase of the present invention has been transformed into a strain of the Escherichia coli which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 25, 1997 under the deposition number DSM 11788.

In a third aspect, the present invention relates to a pectate lyase which is i) a polypeptide produced by Bacillus licheniformis, ATCC 14580, or ii) a polypeptide comprising an amino acid sequence as shown in positions 28–341 of SEQ ID NO: 4, or iii) an analogue of the polypeptide defined in i) or ii) which is at least 45% homologous with said polypeptide, or iv) is derived from said polypeptide by substitution, deletion or addition of one or several amino acids, provided that the arginine in position 233, and optionally also the arginine in position 238, is conserved and the derived polypeptide is at least 42% homologous with said polypeptide, or v) is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having pectate lyase activity and comprising a sequence of nucleotides as shown in SEQ ID NO: 3 from nucleotide 82 to nucleotide 1026; (b) species homologs of (a); (c) polynucleotide molecules that encode a polypeptide having pectate lyase activity that is at least 45% identical to the amino acid sequence of SEQ ID NO: 4 from amino acid residue 28 to amino acid residue 341; (d) molecules complementary to (a), (b) or (c); and (e) degenerate nucleotide sequences of (a), (b), (c) or (d).

The plasmid pSJ1678 comprising the polynucleotide molecule (the DNA sequence) encoding a pectate lyase of the present invention has been transformed into a strain of the Escherichia coli which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 25, 1997 under the deposition number DSM 11789.

In a fourth aspect, the present invention relates to a pectate lyase which is a polypeptide produced by a Bacillus species having the 16S rDNA sequence of SEQ ID NO: 14 or by a Bacillus species having a 16S rDNA sequence homology to SEQ ID NO: 14 higher than 97.3%; ii) a polypeptide comprising an amino acid sequence as shown in positions 181–509 of SEQ ID NO: 6, or iii) an analogue of the polypeptide defined in i) or ii) which is at least 50% homologous with said polypeptide, or iv) is derived from said polypeptide by substitution, deletion or addition of one or several amino acids, provided that the arginine in position 390, and optionally also the arginine in position 395, is conserved and the derived polypeptide is at least 44% homologous with said polypeptide, or v) is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having pectate lyase activity and comprising a sequence of nucleotides as shown in SEQ ID NO: 5 from nucleotide 541 to nucleotide 1530; (b) species homologs of (a); (c) polynucleotide molecules that encode a polypeptide having pectate lyase activity that is at least 50% identical to the amino acid sequence of SEQ ID NO: 6 from amino acid residue 181 to amino acid residue 509; (d) molecules complementary to (a), (b) or (c); and (e) degenerate nucleotide sequences of (a), (b), (c) or (d).

The plasmid pSJ1678 comprising the polynucleotide molecule (the DNA sequence) encoding a pectate lyase of the present invention has been transformed into a strain of the Escherichia coli which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 8, 1998 under the deposition number DSM 12403.

In a fifth aspect, the present invention relates to a pectate lyase which is i) a polypeptide produced by a strain of the species Bacillus halodurans, preferably the species Bacillus sp. KJ59, DSM 12419, or ii) a polypeptide comprising an amino acid sequence as shown in positions 42–348 of SEQ ID NO: 8, or iii) an analogue of the polypeptide defined in i) or ii) which is at least 45% homologous with said polypeptide, or iv) is derived from said polypeptide by substitution, deletion or addition of one or several amino acids, provided that the arginine in position 240, and optionally also the arginine in position 245, is conserved and the derived polypeptide is at least 40% homologous with said polypeptide, or v) is immunologically reactive with a polyclonal antibody raised against said polypeptide in purified form.

The Bacillus sp. KJ59, which is believed to be a strain belonging to or at least very closely related to the known species Bacillus halodurans was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 21 1998 under the deposition number DSM 12419.

Within one aspect, the present invention provides an isolated polynucleotide molecule selected from the group consisting of (a) polynucleotide molecules encoding a polypeptide having pectate lyase activity and comprising a sequence of nucleotides as shown in SEQ ID NO: 7 from nucleotide 124 to nucleotide 1047; (b) species homologs of (a); (c) polynucleotide molecules that encode a polypeptide having pectate lyase activity that is at least 45% identical to the amino acid sequence of SEQ ID NO: 8 from amino acid residue 42 to amino acid residue 348; (d) molecules complementary to (a), (b) or (c); and (e) degenerate nucleotide sequences of (a), (b), (c) or (d).

In a sixth aspect, the present invention relates to a pectate lyase which is a polypeptide produced by a Bacillus species having the 16S rDNA sequence of SEQ ID NO: 13 or by a Bacillus species having a 16S rDNA sequence homology to SEQ ID NO: 13 higher than 98.1%; ii) a polypeptide comprising an amino acid sequence as shown in positions 25–335 of SEQ ID NO: 10, or iii) an analogue of the polypeptide defined in i) or ii) which is at least 45% homologous with said polypeptide, or iv) is derived from said polypeptide by substitution, deletion or addition of one or several amino acids, provided that the arginine in position 227, and optionally also the arginine in position 232, is conserved and the derived polypeptide is at least 41% homologous with said polypeptide, or v) is immunologically reactive with a polyclonal antibody raised against said polypeptide in purified form.

Within one aspect, the present invention provides an isolated polynucleotide molecule selected from the group consisting of (a) polynucleotide molecules encoding a polypeptide having pectate lyase activity and comprising a sequence of nucleotides as shown in SEQ ID NO: 9 from nucleotide 73 to nucleotide 1008; (b) species homologs of (a); (c) polynucleotide molecules that encode a polypeptide having pectate lyase activity that is at least 45% identical to the amino acid sequence of SEQ ID NO: 10 from amino acid residue 25 to amino acid residue 335; (d) molecules complementary to (a), (b) or (c); and (e) degenerate nucleotide sequences of (a), (b), (c) or (d).

The plasmid pSJ1678 comprising the polynucleotide molecule (the DNA sequence) encoding a pectate lyase of the present invention has been transformed into a strain of the Escherichia coli which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 8, 1998 under the deposition number DSM 12404.

Within another aspect of the invention there is provided an expression vector comprising the following operably linked elements: a transcription promoter; a DNA segment selected from the group consisting of a) polynucleotide molecules encoding a polypeptide having pectate lyase activity comprising a nucleotide sequence as shown in SEQ ID NO: 1 from nucleotide 79 to nucleotide 1077, in SEQ ID NO: 3 from nucleotide 82 to nucleotide 1026, in SEQ ID NO: 5 from nucleotide 541 to nucleotide 1530, in SEQ ID NO: 7 from nucleotide 124 to nucleotide 1047 or as shown in SEQ ID NO: 9 from nucleotide 73 to nucleotide 1008, b) polynucleotide molecules encoding a polypeptide having pectate lyase activity that is at least 50% identical to the amino acid sequence of SEQ ID NO: 2 from amino acid residue 27 to amino acid residue 359, of SEQ ID NO: 4 from amino acid residue 28 to amino acid residue 341, of SEQ ID NO: 6 from amino acid residue 181 to amino acid residue 509, of SEQ ID NO: 8 from amino acid residue 42 to amino acid residue 348 or to the amino acid sequence of SEQ ID NO: 10 from amino acid residue 25 to amino acid residue 335, and (c) degenerate nucleotide sequences of (a) or (b); and a transcription terminator.

Within yet another aspect of the present invention there is provided a cultured cell into which has been introduced an expression vector as disclosed above, wherein said cell expresses the polypeptide encoded by the DNA segment.

A further aspect of the present invention provides an isolated polypeptide having pectate lyase activity selected from the group consisting of a) polypeptide molecules having pectate lyase activity and comprising an amino acid sequence as shown in SEQ ID NO: 2 from residue 27 to residue 359; b) polypeptide molecules having pectate lyase activity and which are at least 45% identical to the amino acids of SEQ ID NO: 2 from amino acid residue 27 to amino acid residue 359; c) polypeptide molecules having pectate lyase activity and comprising an amino acid sequence as shown in SEQ ID NO: 4 from residue 28 to residue 241; d) polypeptide molecules having pectate lyase activity and which are at least 45% identical to the amino acids of SEQ ID NO: 4 from amino acid residue 28 to amino acid residue 341; e) polypeptide molecules having pectate lyase activity and comprising an amino acid sequence as shown in SEQ ID NO: 6 from residue 181 to residue 509; f) polypeptide molecules having pectate lyase activity and which are at least 50% identical to the amino acids of SEQ ID NO: 6 from amino acid residue 181 to amino acid residue 509; g) polypeptide molecules having pectate lyase activity and comprising an amino acid sequence as shown in SEQ ID NO: 8 from residue 42 to residue 348; h) polypeptide molecules having pectate lyase activity and which are at least 45% identical to the amino acids of SEQ ID NO: 8 from amino acid residue 42 to amino acid residue 348; i) polypeptide molecules having pectate lyase activity and comprising an amino acid sequence as shown in SEQ ID NO: 10 from residue 25 to residue 335; k) polypeptide molecules having pectate lyase activity and which are at least 45% identical to the amino acids of SEQ ID NO: 10 from amino acid residue 25 to amino acid residue 335; and l) species homologs of a), b), c), d), e), f), g), h), i) and k).

Within another aspect of the present invention there is provided a composition comprising a purified pectate lyase according to the invention in combination with other polypeptides having enzymatic activity.

Within another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

The novel pectate lyase enzymes of the present invention are useful for the treatment of cellulosic material, especially cellulose-containing fiber, yarn, woven or non-woven fabric, treatment of mechanical paper-making pulps or recycled waste paper, and for retting of fibers. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising an enzyme having substantial pectate lyase activity; and to use of the enzyme of the invention for the treatment of cellulose-containing fibers, yarn, woven or non-woven fabric.

The pectate lyases of the invention are very effective for use in an enzymatic scouring process in the preparation of cellulosic material e.g. for proper response in subsequent dyeing operations. Further, it is contemplated that detergent compositions comprising the novel pectate lyases are capable of removing or bleaching certain soils or stains present on laundry, especially soils and spots resulting from galactan or arabinogalactan containing food, plants, and the like. It is also contemplated that treatment with detergent compositions comprising the novel enzyme can prevent binding of certain soils to the cellulosic material. The enzymes of the invention are also useful as ingredients in hard surface cleaning compositions having the effect of removing or assisting in removing certain soils or stains from hard surfaces in need of cleaning.

BRIEF DESCRIPTION OF THE DRAWINGS

FIG. 1 shows a sequence alignment of the mature parts of the amino acid sequences of SEQ ID NOS: 2, 4, 6, 8 and 10, the alignment numbered from 1 to 344. For example, position 223 of the alignment numbering corresponds to position 240 of SEQ ID NO: 2, to position 233 of SEQ ID NO: 4, to position 390 of SEQ ID NO: 6, to position 240 of SEQ ID NO: 8 and to position 227 of SEQ ID NO: 10.

DEFINITIONS

Figure 2:
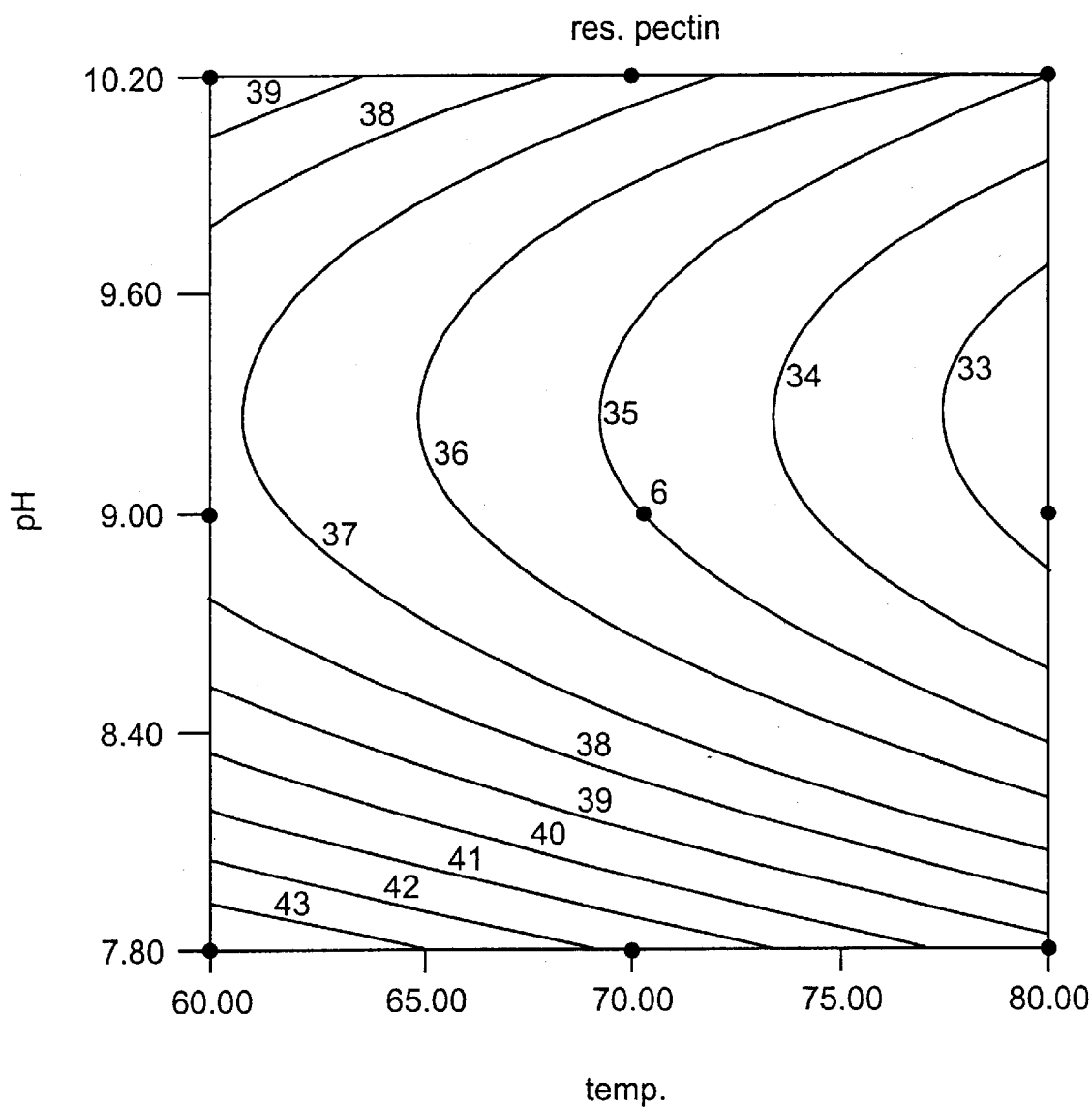
FIG. 2 is a graphic illustration of the effect of pH and temperature on the removal of pectin from a cotton fabric using a thermostable pectate lyase. The removal of pectin is expressed as % residual pectin. The pectate lyase was applied to the fabric at a dosage of 100 micromol/min/kg fabric.

Prior to discussing this invention in further detail, the following terms will first be defined The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "endogeneous to" as used herein in connection with a specific microbial source, means that a polypeptide is produced by the specific source due to the presence in the source of a native gene, ie a gene which has not been recombinantly inserted into a cell of the source but is naturally occurring.

The term "operably linked", when referring to DNA segments, denotes that the segments are arranged so that they function in concert for their intended purposes, e.g. transcription initiates in the promoter and proceeds through the coding segment to the terminator The term "polynucleotide" denotes a single- or double-stranded polymer of deoxyribonucleotides or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "pectin" denotes pectate, polygalacturonic acid, and pectin which may be esterified to a higher or lower degree.

The term "pectinase" denotes a pectinase enzyme defined according to the art where pectinases are a group of enzymes that cleave glycosidic linkages of pectic substances mainly poly(1,4-alpha-D-galacturonide and its derivatives (see reference Sakai et al., Pectin, pectinase and protopectinase: production, properties and applications, pp 213–294 in: Advances in Applied Microbiology vol:39, 1993).

Preferably a pectinase of the invention is a pectinase enzyme which catalyzes the random cleavage of alpha-1,4-glycosidic linkages in pectic acid also called polygalacturonic acid by transelimination such as the enzyme class polygalacturonate lyase (EC 4.2.2.2) (PGL) also known as poly(1,4-alpha-D-galacturonide) lyase also known as pectate lyase.

DETAILED DESCRIPTION OF THE INVENTION

HOW TO USE A SEQUENCE OF THE INVENTION TO GET OTHER RELATED SEQUENCES: The disclosed sequence information herein relating to a polynucleotide sequence encoding a pectate lyase of the invention can be used as a tool to identify other homologous pectate lyases. For instance, polymerase chain reaction (PCR) can be used to amplify sequences encoding other homologous pectate lyases from a variety of microbial sources, in particular of different Bacillus species.
Polynucleotides:

Within preferred embodiments of the invention an isolated polynucleotide of the invention will hybridize to similar sized regions of SEQ ID NO: 1, 3, 5, 7 or 9, respectively, or a sequence complementary thereto, under at least medium stringency conditions.

In particular polynucleotides of the invention will hybridize to a denatured double-stranded DNA probe comprising either the full sequence (encoding for the mature part of the polypeptide) shown in positions 79–1077 of SEQ ID NO: 1, in positions 82–1026 of SEQ ID NO: 3, in positions 541–1530 of SEQ ID NO: 5, in positions 124–1047 of SEQ ID NO: 7 or in positions 73–1008 of SEQ ID NO: 9, or any probe comprising a subsequence of SEQ ID NO: 1, 3, 5, 7 or 9, respectively, or any probe comprising a subsequence of SEQ ID NO: 1, 3, 5, 7 or 9 having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×109 cpm/micro-g) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using an x-ray film.

As previously noted, the isolated polynucleotides of the present invention include DNA and RNA. Methods for isolating DNA and RNA are well known in the art. DNA and RNA encoding genes of interes can be cloned in Gene Banks or DNA libraries by means of methods known in the art.

Polynucleotides encoding polypeptides having pectate lyase activity of the invention are then identified and isolated by, for example, hybridization or PCR.

The present invention further provides counterpart polypeptides and polynucleotides from different bacterial strains (orthologs or paralogs). Of particular interest are pectate lyase polypeptides from gram-positive alkalophilic strains, including species of Bacillus.

Species homologues of a polypeptides pectate lyase activity of the invention can be cloned using information and compositions provided by the present invention in combination with conventional cloning techniques. For example, DNA can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA encoding a polypeptide having pectate lyase activity of the invention can then be isolated by a variety of methods, such as by probing with a complete or partial DNA or with one or more sets of degenerate probes based on the disclosed sequences. A DNA can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (mono-clonal or polyclonal) raised against the pectate lyase cloned from *B. licheniformis*, ATCC 14580, the pectate lyase cloned from *B. agaradhaerens*, NCIMB 40482, or the pectate lyase cloned from Bacillus sp. AAI12 identified by its 16S rDNA sequence listed in SEQ ID NO: 14, or the pectate lyase cloned from Bacillus sp. KJ59, DSM 12419, or the pectate lyase cloned from Bacillus sp. I534 identified by its 16S rDNA sequence listed in SEQ ID NO: 13 all of which are expressed and purified as described in Materials and Methods and the Examples, or by an activity test relating to a polypeptide having pectate lyase activity. Similar techniques can also be applied to the isolation of genomic clones.

The polypeptide encoding part of the DNA sequence cloned into plasmid pSJ1678 present in *Escherichia coli* DSM 11789 and/or an analogue DNA sequence of the invention may be cloned from a strain of the bacterial species *Bacillus licheniformis*, preferably the strain ATCC 14580, producing the pectate lyase enzyme, or another or related organism as described herein.

Similarly, the polypeptide encoding part of the DNA sequence cloned into plasmid pSJ1678 present in *Escheri-*

*chia coli* DSM 11789 and/or an analogue DNA sequence of the invention may be cloned from a strain of the bacterial species *Bacillus agaradhaerens* as represented by the type strain DSM 8721, producing the pectate lyase enzyme, or another or related organism as described herein. Also, the polypeptide encoding part of the DNA sequence cloned into plasmid pSJ1678 present in *Escherichia coli* DSM 12403 and 12404, respectively, and/or an analogue DNA sequence of the invention may be cloned from a strain of Bacillus sp. AAI12, Bacillus sp. KJ59, DSM 12419, or Bacillus sp. I534 producing the pectate lyase enzyme, or another or related organism as described herein.

Alternatively, the analogous sequence may be constructed on the basis of the DNA sequence obtainable from the plasmid present in *Escherichia coli* DSM 11788, 11789, DSM 12403 and 12404, e.g be a sub-sequence thereof, and/or by introduction of nucleotide substitutions which do not give rise to another amino acid sequence of the pectat lyase encoded by the DNA sequence, but which corresponds to the codon usage of the host organism intended for production of the enzyme, or by introduction of nucleotide substitutions which may give rise to a different amino acid sequence (i.e. a variant of the pectate lyase of the invention).

Based on the sequence information disclosed herein a full length DNA sequence encoding a pectinase of the invention and comprising the DNA sequence shown in SEQ ID No 1, 3, 5, 7 or 9, respectively, may be cloned.

Cloning of is performed by standard procedures known in the art such as by, preparing a genomic library from a Bacillus strain;

plating such a library on suitable substrate plates;

identifying a clone comprising a polynucleotide sequence of the invention by standard hybridization techniques using a probe based on SEQ ID No 1, 3, 5, 7 or 9, respectively; or by identifying a clone from e.g. the *Bacillus licheniformis* ATCC 14580 or the *Bacillus agaradhaerens* DSM 8721 or a highly related Bacillus genomic library by an Inverse PCR strategy using primers based on sequence information from SEQ ID No 1, 3, 5, 7 or 9, respectively. Reference is made to M. J. MCPherson et al. ("PCR A practical approach" Information Press Ltd, Oxford England) for further details relating to Inverse PCR.

Based on the sequence information disclosed herein (SEQ ID NOS: 1, 2, 3, 4, 5, 6, 7, 8, 9 and 10) is it routine work for a person skilled in the art to isolate homologous polynucleotide sequences encoding homologous pectinases of the invention by a similar strategy using genomic libraries from related microbial organisms, in particular from genomic libraries from other strains of the genus Bacillus such as *Bacillus subtilis*.

Alternatively, the DNA encoding the pectat lyase of the invention may, in accordance with well-known procedures, conveniently be cloned from a suitable source, such as any of the below mentioned organisms, by use of synthetic oligonucleotide probes prepared on the basis of the DNA sequence obtainable from the plasmid present in *Escherichia coli* DSM 11788, DSM 11789, DSM 12403 or DSM 12404.

Accordingly, the polynucleotide molecule of the invention may be isolated from *Escherichia coli,* DSM 11788, DSM 11789, DSM 12403 or DSM 12404, in which the each of the plasmids obtained by cloning such as described above is deposited. Also, the present invention relates to an isolated substantially pure biological culture of each of the strains *Escherichia coli,* DSM 11788, DSM 11789, DSM 12403 and DSM 12404, respectively.

Polypeptides:

The sequence of amino acids no. 27–359 of SEQ ID No 2 is a mature pectate lyase sequence; positions 1–26 is a propeptide. The sequence of amino acids no. 28–341 of SEQ ID No 4 is a mature pectate lyase sequence; positions 1–27 is a propeptide. The sequence of amino acids no. 181–509 of SEQ ID No 6 is a mature pectate lyase sequence; positions 1–31 is a transit peptide; positions 32–86 is a first lectin domain; positions 87–134 is a second lectin domain; positions 135–180 is a third lectin domain. The sequence of amino acids no. 42–348 of SEQ ID No 8 is a mature pectate lyase sequence; positions 1–41 is a propeptide. The sequence of amino acids no. 25–335 of SEQ ID No 10 is a mature pectate lyase sequence; positions 1–24 is a propeptide. It is believed that the pectate lyases of the invention belong to family 1 of polysaccharide lyases.

The present invention also provides pectate lyase polypeptides that are substantially homologous to the mature polypeptides of SEQ ID NO: 2, 4, 6, 8 and 10 and their species homologs (paralogs or orthologs). The term "substantially homologous" is used herein to denote polypeptides having at least 45% preferably at least 50%, preferably at least 60%, more preferably at least 70%, more preferably at least 85%, and even more preferably at least 90%, sequence identity to the sequences shown in SEQ ID NOS: 2, 4, 6, 8 and 10, or their orthologs or paralogs. Such polypeptides will more preferably be at least 95% identical, and most preferably 98% or more identical to the sequences shown in SEQ ID NOS: 2, 4, 6, 8 and 10, or their orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

The pectate lyases of the invention comprising the unique first amino acid sequence NLNSRVP (SEQ ID NO: 2), which is believed to be unique and thereby sufficient for identifying any new pectate lyase belonging to this novel group of pectate lyase of the present invention having excellent performance in industrial processes such as textile treatment and laundering, are preferably derived from a microorganism, preferably from a bacterium, an archea or a fungus, especially from a bacterium such as a bacterium belonging to Bacillus, preferably to an alkalophilic Bacillus strain which may be selected from the group consisting of the species *Bacillus licheniformis, Bacillus agaradhaerens, Bacillus halodurans* and the Bacillus species I534 and AAI12 identified by the 16S rDNA sequence listed as SEQ ID NO: 13 or 14, respectively, and other Bacillus species which are highly related to any of these species based on aligned 16S rDNA sequences as explained below, preferably species which are at least 97%, even more preferably at least 98%, homologous to each of these species.

These highly related Bacillus species are found based on phylogenic relationships identified using aligned published 16S rDNA sequences available through the ARB sequence database (release from 04-Mar-97 available at http://www.biol.chemie.tu-muenchen.de/pub/ARB/data/). Sequence analysis was performed using the ARB program package (Strunck, O. and Ludwig, W. 1995. ARB—a software environment for sequence data. Department of Microbiology, University of Munich, Munich, Germany. email arb@mikro.biologie.tu-muenchen.de, or available via the www. at http://www.biol.chemie.tu-muenchen.de/pub/ARB/). The alignment was based on secondary structure, and performed using the automatic alignment function (version 2.0) of the ARB alignment (ARB_EDIT4) including manual evaluation.

Sequence similarities were established using the Phylip Distance Matrix option (with default settings, i.e. no corrections) integrated in the ARB program package, by converting the distances to percent sequence similarity. Accordingly, the species most closely related to *B. licheniformis*, ATCC 14580, is *B. subtilis;* the species most closely related to Bacillus sp. KJ59, DSM 12419, is *B. halodurans*, DSM 8718 (16S data X76442) which is so close that the strain KJ59 is believed to be a strain of this species; the species most closely related to Bacillus sp. AAI12 is *B. alcalophilus*, DSM 485 (16S data X76436) which shows a 16S homology of 97.3%; and the species most closely related to Bacillus sp. I534 is Bacillus sp. PN1, DSM 8714 (16S data X76438) which shows a 16S homology of 98.1%.

Phylogenetic trees were calculated using the ARB program by the maximum likelihood method (FastDnaML algorithm from G. J. Olsen, H. Matsuda, R. Hagstrom, and R. Overbeek. fastDNAml: a tool for construction of phylogenetic trees of DNA sequences using maximum likelihood. Comput.Appl.Biosci. 10 (1):41–48, 1994.) using default settings (no filter and no weighting mask).

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a Pectate lyase polypeptide of the invention.

TABLE 1

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |

TABLE 1-continued

Conservative amino acid substitutions

| | |
|---|---|
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the pectate lyase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e pectate lyase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (Science 241:53–57, 1988), Bowie and Sauer (*Proc. Natl. Acad. Sci. USA* 86:2152–2156, 1989), WO 95/17413, or WO 95/22625. Briefly, these authors disclose methods for simultaneously randomizing two or more positions in a polypeptide, or recombination/shuffling of different mutations (WO 95/17413, WO 95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 27 to 359 of SEQ ID NO: 2, to residues 28 to 341 of SEQ ID NO: 4, to residues 181 to 509 of SEQ ID NO: 6, to residues 42 to 348 of SEQ ID NO: 8 and to residues 25 to 335 of SEQ ID NO: 10 and retain the pectate lyase activity of the wild-type protein.

Such variants of the invention are pectate lyases having, in position 223 relative to the numbering in the sequence alignment of FIG. 1, the amino acid residue arginine. In a preferred embodiment, such variant also holds a conserved arginine in position 228 relative to the numbering in the sequence alignment of FIG. 1. Accordingly, the present invention relates to pectate lyases having an amino acid sequence which is derived from any of the amino acid sequences SEQ ID No: 2, 4, 6, 8 and 10 by deletion, replacement or addition of one or more amino acid residues (hereinafter referred to as mutation) provided that the pectate lyase activity is not deactivated and the mutation conserves arginine at the 223rd position and optionally also arginine at the 228th position of the sequence numbering in the alignment of FIG. 1. These positions corresponds to arginine (R) at the 240th position and at the 245th position in SEQ ID No: 2, to positions 233 and 238 in SEQ ID NO: 4, to positions 390 and 395 in SEQ ID NO: 6, to positions 240 and 245 in SEQ ID NO: 8, and to positions 227 and 232 in SEQ ID NO: 10.

Further, in addition to the above conserved arginines, the mutation preferably conserves aspartic acid (D) at the 169th position and/or aspartic acid (D) at the 173rd position and/or lysine (K) at the 193rd position of the sequence numbering in the alignment of FIG. 1. These positions corresponds to aspartic acid (D) at the at the 186th position and at the 190th position and lysine (K) at the 210th position in SEQ ID NO: 2; to positions D180, D184 and K204 in SEQ ID NO: 4; to positions D336, D340 and K360 in SEQ ID NO: 6; to positions D187, D191 and K211 in SEQ ID NO: 8, and to positions D174, D178 and K198 in SEQ ID NO: 10. In a further embodiment of the invention, there is provided mutants of the parent mature polypeptides of any of the sequences listed in SEQ ID NOS: 2, 4, 6, 8 and 10, the mutants being active pectate lyases having the aspartic acids in the positions specified above replaced with an amino acid residue selected from the group consisting of glutamic acid (E), serine (S) and threonine (T), i.e. the following mutations: D169E, D169S, D169T, D173E, D173S, D173T (FIG. 1 alignment numbering).

Also, the degree of mutation is not particularly limited provided that the above-described arginine in the 223rd position position is conserved. Preferably, 40% or higher homology exists between such mutation variants of the native or parent pectate lyase enzyme, calculated on the any of the sequence SEQ ID NOS: 2, 4, 6, 8 and 10: 42% or higher homology exists between amino acid positions 39 and 359 of SEQ ID NO: 2 and amino acid positions 46 and 341 of SEQ ID NO: 4; 44% or higher homology exists between amino acid positions 187 and 509 of SEQ ID NO: 6; 40% or higher homology exists between amino acid positions 50 and 348 of SEQ ID NO: 8; and 41% or higher homology exists between amino acid positions 40 and 335 of SEQ ID NO: 10. Preferably, the homology is at least 45%, preferably at least 50%, more preferably at least 55%, more preferably at least 60%, even more preferably at least 70%, even more preferably at least 75%, even more preferably at least 80%, even more preferably at least 85%, even more preferably at least 90%, even more preferably at least 95%, especially at least 98%.

The pectate lyase of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part of the encoded enzyme, or a CBD from another origin may be introduced into the pectin degrading enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the pectin degrading enzyme and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of the pectin degrading enzyme of the invention.

Preferably, the enzyme of the present invention has its maximum catalytic activity at a pH of at least 8, more preferably higher than 8.5, more preferably higher than 9, more preferably higher than 9.5, more preferably higher than 10, even more preferably higher than 10.5, especially higher than 11; and preferably the maximum activity of the enzyme is obtained at a temperature of at least 50° C., more preferably of at least 55° C.

Protein Production:

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus agaradhaerens or Bacillus licheniformis.

Techniques for manipulating cloned DNA molecules and introducing exogenous DNA into a variety of host cells are disclosed by Sambrook et al., Molecular Cloning: A Laboratory Manual, 2nd ed., Cold Spring Harbor Laboratory Press, Cold Spring Harbor, N.Y., 1989; Ausubel et al. (eds.), Current Protocols in Molecular Biology, John Wiley and Sons, Inc., N.Y., 1987; and (Bacillus subtilis and Other Gram-Positive Bacteria, Sonensheim et al., 1993, American Society for Microbiology, Washington D.C.), which are incorporated herein by reference.

In general, a DNA sequence encoding a pectate lyase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. Numerous suitable secretory signal sequences are known in the art and reference is made to (Bacillus subtilis and Other Gram-Positive Bacteria, Sonensheim et al., 1993, American Society for Microbiology, Washington D.C.; and Cutting, S. M.(eds.) "Molecular Biological Methods for Bacillus". John Wiley and Sons, 1990) for further description of suitable secretory signal sequences especially for secretion in a Bacillus host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The polypeptides of the present invention may also be produced by fermenting a wildtype strain belonging to the genus Bacillus, preferably a strain which may be selected from the group consisting of the species Bacillus licheniformis, Bacillus agaradhaerens and highly related Bacillus species in which all species are at least 95% homologous to Bacillus licheniformis based on aligned 16S rDNA sequences. Specific and highly preferred examples are Bacillus licheniformis, ATCC 14580, and Bacillus agaradhaerens, DSM 8721.

Further, the polypeptides of the present invention may be produced by fermenting a mutant or a variant derived from the above mentioned strain. Such a mutant may be obtained by using conventional mutagenesis by subjecting the strain in question to treatment with a mutagen (eg NTG (n-methyl-N-nitro-N-nitrosoguanidine)) or to ultraviolet radiation, eg as described in Manual of methods for General Bacteriology; ASM 1981, Chapter 13. This mutagenesis is performed to stimulate mutation of the strains. Following mutagenesis a screening for mutants giving higher pectinase yields aer possible using conventional plate assays or liquid assays.

The fermentation may be carried out by cultivation of the strain under aerobic conditions in a nutrient medium containing carbon and nitrogen sources together with other essential nutrients, the medium being composed in accordance with the principles of the known art. The medium may be a complex rich medium or a minimal medium. The nitrogen source may be of inorganic and/or organic nature. Suitable inorganic nitrogen sources are nitrates and ammonium salts. Among the organic nitrogen sources quite a number are used regularly in fermentations. Examples are soybean meal, casein, corn, corn steep liquor, yeast extract, urea and albumin. Suitable carbon sources are carbohydrates or carbohydrate containing materials. Preferable the nutrient medium contains pectate, polygalacturonic acid and/or pectin esterified to a higher or lower degree as carbon source and/or inducer of pectinase production. Alternatively, the medium contains a pectin rich material such as soybean meal, apple pulp or citrus peel.

Since the Bacillus species of this invention are alkalophilic the cultivation is preferably conducted at alkaline pH values such as at least pH 8 or at least pH 9, which can be obtained by addition of suitable buffers such as sodium carbonate or mixtures of sodium carbonate and sodium bicarbonate after sterilisation of the growth medium.

It is contemplated that fermentation of a wildtype strain or mutant in a suitable medium can result in a yield of at least 0.5 g of pectinase protein per liter of culture broth or even at least 1 g/l or 2 g/l.

Protein Isolation:

When the expressed recombinant polypeptide is secreted the polypeptide may be purified from the growth media. Preferably the expression host cells are removed from the media before purification of the polypeptide (e.g. by centrifugation).

When the expressed recombinant polypeptide is not secreted from the host cell, the host cell are preferably disrupted and the polypeptide released into an aqueous "extract" which is the first stage of such purification techniques. Preferably the expression host cells are removed from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) is secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

Transgenic Plants

The present invention also relates to a transgenic plant, plant part or plant cell which has been transformed with a DNA sequence encoding the pectin degrading enzyme of the invention so as to express and produce this enzyme in recoverable quantities. The enzyme may be recovered from the plant or plant part. Alternatively, the plant or plant part containing the recombinant enzyme may be used as such.

The transgenic plant can be dicotyledonous or monocotyledonous, for short a dicot or a monocot. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism Arabidopsis thaliana.

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the enzyme of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, eg on the basis of when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are eg described by Tague et al, Plant, Phys., 86, 506, 1988.

For constitutive expression the 35S-CaMV promoter may be used (Franck et al., 1980. Cell 21: 285–294). Organspecific promoters may eg be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–889 (1998)), a *Vicia faba* promoter from the legumin B4 and the unknown seed protein gene from *Vicia faba* described by Conrad U. et al, Journal of Plant Physiology Vol. 152, No. 6 pp. 708–711 (1998), a promotter from a seed oil body protein (Chen et al., Plant and cell physiology vol. 39, No. 9 pp. 935–941 (1998), the storage protein napA promoter from *Brassica napus,* or any other seed specific promoter known in the art, eg as described in WO 91/14772. Furthermore, the promoter may be a leaf specific promoter such as the rbcs promoter from rice or tomato (Kyozuka et al., Plant Physiology Vol. 102, No. 3 pp. 991–1000 (1993), the chlorella virus adenine methyltransferase gene promoter (Mitra, A. and Higgins, D W, Plant Molecular Biology Vol. 26, No. 1 pp. 85–93 (1994), or the aldP gene promoter from rice (Kagaya et al., Molecular and General Genetics Vol. 248, No. 6 pp. 668–674 (1995), or a wound inducible promoter such as the potato pin2 promoter (Xu et al, Plant Molecular Biology Vol. 22, No. 4 pp. 573–588 (1993).

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including Agrobacterium-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275–281; Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well known in the art.

Enzyme Preparation

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant pectate lyase, but which microorganism simultaneously produces other enzymes, e.g. pectin lyases, proteases, or cellulases, being naturally occurring fermentation products of the microorganism, i.e. the enzyme complex conventionally produced by the corresponding naturally occurring microorganism.

The pectate lyase preparation of the invention may further comprise one or more enzymes selected from the group consisting of proteases, cellulases (endo-beta-1,4-glucanases), beta-glucanases (endo-beta-1,3(4)-glucanases), lipases, cutinases, peroxidases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are mono-component enzyme(s) which is/are mixed with the other enzyme(s) to form an enzyme preparation with the desired enzyme blend.

Immunological Cross-Reactivity

Polyclonal antibodies (which are monospecific for a given enzyme protein) to be used in determining immunological cross-reactivity may be prepared by use of a purified pectate lyase enzyme. More specifically, antiserum against the pectate lyase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Use in the Detergent or Cleaning Industry

In further aspects, the present invention relates to a detergent composition comprising the pectate lyase enzyme or enzyme preparation of the invention, to a process for machine treatment of fabrics comprising treating fabric during a washing cycle of a machine washing process with a washing solution comprising the pectate lyase enzyme or enzyme preparation of the invention, and to cleaning compositions, including laundry, hard surface cleaner, personal cleansing and oral/dental compositions, comprising a pectate lyase enzyme or enzyme preparation of the invention providing superior cleaning performance, i.e. superior stain removal.

Without being bound to this theory, it is believed that the mannanase of the present invention is capable of effectively degrading or hydrolysing any soiling or spots containing galatomannans and, accordingly, of cleaning laundry comprising such soilings or spots.

The cleaning compositions of the invention must contain at least one additional detergent component. The precise nature of these additional components, and levels of incorporation thereof will depend on the physical form of the composition, and the nature of the cleaning operation for which it is to be used.

The cleaning compositions of the present invention preferably further comprise a detergent ingredient selected from a selected surfactant, another enzyme, a builder and/or a bleach system.

The cleaning compositions according to the invention can be liquid, paste, gels, bars, tablets, spray, foam, powder or granular. Granular compositions can also be in "compact" form and the liquid compositions can also be in a "concentrated" form.

The compositions of the invention may for example, be formulated as hand and machine dishwashing compositions, hand and machine laundry detergent compositions including laundry additive compositions and compositions suitable for use in the soaking and/or pretreatment of stained fabrics, rinse added fabric softener compositions, and compositions for use in general household hard surface cleaning operations. Compositions containing such carbohydrases can also be formulated as sanitization products, contact lens cleansers and health and beauty care products such as oral/dental care and personal cleaning compositions.

When formulated as compositions for use in manual dishwashing methods the compositions of the invention preferably contain a surfactant and preferably other detergent compounds selected from organic polymeric compounds, suds enhancing agents, group II metal ions, solvents, hydrotropes and additional enzymes.

When formulated as compositions suitable for use in a laundry machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components. Such compositions containing carbohydrase can provide fabric cleaning, stain removal, whiteness maintenance, softening, colour appearance, dye transfer inhibition and sanitization when formulated as laundry detergent compositions.

The compositions of the invention can also be used as detergent additive products in solid or liquid form. Such additive products are intended to supplement or boost the performance of conventional detergent compositions and can be added at any stage of the cleaning process.

If needed the density of the laundry detergent compositions herein ranges from 400 to 1200 g/liter, preferably 500 to 950 g/liter of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulphates and chlorides. A preferred filler salt is sodium sulphate.

Liquid detergent compositions according to the present invention can also be in a "concentrated form", in such case, the liquid detergent compositions according the present invention will contain a lower amount of water, compared to conventional liquid detergents. Typically the water content of the concentrated liquid detergent is preferably less than 40%, more preferably less than 30%, most preferably less than 20% by weight of the detergent composition.

Suitable specific detergent compounds for use herein are selected from the group consisting of the specific compounds as described in WO 97/01629 which is hereby incorporated by reference in its entirety.

Mannanase may be incorporated into the cleaning compositions in accordance with the invention preferably at a level of from 0.0001% to 2%, more preferably from 0.0005% to 0.5%, most preferred from 0.001% to 0.1% pure enzyme by weight of the composition.

The cellulases usable in the present invention include both bacterial or fungal cellulases. Preferably, they will have a pH optimum of between 5 and 12 and a specific activity above 50 CEVU/mg (Cellulose Viscosity Unit). Suitable cellulases are disclosed in U.S. Pat. No. 4,435,307, J61078384 and WO 96/02653 which discloses fungal cellulase produced from *Humicola insolens,* Trichoderma, Thielavia and Sporotrichum, respectively. EP 739 982 describes cellulases isolated from novel Bacillus species. Suitable cellulases are also disclosed in GB-A-2075028; GB-A-2095275; DE-OS-22 47 832 and WO 95/26398.

Examples of such cellulases are cellulases produced by a strain of *Humicola insolens* (*Humicola grisea* var. *thermoidea*), particularly the strain *Humicola insolens,* DSM 1800. Other suitable cellulases are cellulases originated from *Humicola insolens* having a molecular weight of about 50 kD, an isoelectric point of 5.5 and containing 415 amino acids; and a ~43 kD endo-beta-1,4-glucanase derived from *Humicola insolens,* DSM 1800; a preferred cellulase has the amino acid sequence disclosed in PCT Patent Application No. WO 91/17243. Also suitable cellulases are the EGIII cellulases from *Trichoderma longibrachiatum* described in WO 94/21801. Especially suitable cellulases are the cellulases having color care benefits. Examples of such cellulases are the cellulases described in WO 96/29397, EP-A-0495257, WO 91/17243, WO 91/17244 and WO 91/21801. Other suitable cellulases for fabric care and/or cleaning properties are described in WO 96/34092, WO 96/17994 and WO 95/24471.

Said cellulases are normally incorporated in the detergent composition at levels from 0.0001% to 2% of pure enzyme by weight of the detergent composition.

Preferred cellulases for the purpose of the present invention are alkaline cellulases, i.e. enzyme having at least 25%, more preferably at least 40% of their maximum activity at a pH ranging from 7 to 12. More preferred cellulases are enzymes having their maximum activity at a pH ranging from 7 to 12. A preferred alkaline cellulase is the cellulase sold under the tradename Carezyme® by Novo Nordisk A/S.

Amylases (alpha and/or beta) can be included for removal of carbohydrate-based stains. WO 94/02597, Novo Nordisk A/S published Feb. 3, 1994, describes cleaning compositions which incorporate mutant amylases. See also WO 95/10603, Novo Nordisk A/S, published Apr. 20, 1995. Other amylases known for use in cleaning compositions include both alpha- and beta-amylases. Alpha-amylases are known in the art and include those disclosed in U.S. Pat. No. 5,003,257; EP 252,666; WO 91/00353; FR 2,676,456; EP 285,123; EP 525,610; EP 368,341; and British Patent specification no. 1,296,839 (Novo). Other suitable amylases are stability-enhanced amylases described in WO 94/18314, published Aug. 18, 1994 and WO 96/05295, Genencor, published Feb. 22, 1996 and amylase variants having additional modification in the immediate parent available from Novo Nordisk A/S, disclosed in WO 95/10603, published April 95. Also suitable are amylases described in EP 277 216, WO 95/26397 and WO 96/23873 (all by Novo Nordisk).

Examples of commercial alpha-amylases products are Purafect Ox Am® from Genencor and Termamyl®, Ban®, Fungamyl® and Duramyl®, all available from Novo Nordisk A/S Denmark. WO 95/26397 describes other suitable amylases: alpha-amylases characterized by having a specific activity at least 25% higher than the specific activity of Termamyl® at a temperature range of 25° C. to 55° C. and at a pH value in the range of 8 to 10, measured by the Phadebas® alpha-amylase activity assay. Suitable are variants of the above enzymes, described in WO 96/23873 (Novo Nordisk). Other amylolytic enzymes with improved properties with respect to the activity level and the combination of thermostability and a higher activity level are described in WO 95/35382.

Preferred amylases for the purpose of the present invention are the amylases sold under the tradename Termamyl, Duramyl and Maxamyl and or the alpha-amylase variant demonstrating increased thermostability disclosed as SEQ ID NO: 2 in WO 96/23873.

Preferred amylases for specific applications are alkaline amylases, i.e. enzymes having an enzymatic activity of at least 10%, preferably at least 25%, more preferably at least 40% of their maximum activity at a pH ranging from 7 to 12.

More preferred amylases are enzymes having their maximum activity at a pH ranging from 7 to 12.

The amylolytic enzymes are incorporated in the detergent compositions of the present invention a level of from 0.0001% to 2%, preferably from 0.00018% to 0.06%, more preferably from 0.00024% to 0.048% pure enzyme by weight of the composition.

The term xyloglucanase encompasses the family of enzymes described by Vincken and Voragen at Wageningen University [Vincken et al (1994) Plant Physiol., 104, 99–107] and are able to degrade xyloglucans as described in Hayashi et al (1989) Plant. Physiol. Plant Mol. Biol., 40, 139–168. Vincken et al demonstrated the removal of xyloglucan coating from cellulase of the isolated apple cell wall by a xyloglucanase purified from *Trichoderma viride* (endo-IV-glucanase). This enzyme enhances the enzymatic degradation of cell wall-embedded cellulose and work in synergy with pectic enzymes. Rapidase LIQ+ from Gist-Brocades contains a xyloglucanase activity.

This xyloglucanase is incorporated into the cleaning compositions in accordance with the invention preferably at a level of from 0.0001% to 2%, more preferably from 0.0005% to 0.5%, most preferred from 0.001% to 0.1% pure enzyme by weight of the composition.

Preferred xyloglucanases for specific applications are alkaline xyloglucanases, ie enzymes having an enzymatic activity of at least 10%, preferably at least 25%, more preferably at least 40% of their maximum activity at a pH ranging from 7 to 12. More preferred xyloglucanases are enzymes having their maximum activity at a pH ranging from 7 to 12.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein or genetic engineering techniques in order to optimize their performance efficiency in the cleaning compositions of the invention. For example, the variants may be designed such that the compatibility of the enzyme to commonly encountered ingredients of such compositions is increased. Alternatively, the variant may be designed such that the optimal pH, bleach or chelant stability, catalytic activity and the like, of the enzyme variant is tailored to suit the particular cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing metal binding sites to increase chelant stability.

Use in the Textile and Cellulosic Fiber Processing Industries

The pectate lyase of the present invention can be used in combination with other carbohydrate degrading enzymes (for instance arabinanase, xyloglucanase, pectinase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of the primary cell wall or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The preparation of the present invention is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are a. Desizing (for woven goods) using polymeric size like e.g. starch, CMC or PVA is added before weaving in order to increase the warp speed; This material must be removed before further processing.

b. Scouring, the aim of which is to remove non-cellulosic material from the cotton fiber, especially the cuticle (mainly consisting of waxes) and primary cell wall (mainly consisting of pectin, protein and xyloglucan). A proper wax removal is necessary for obtaining a high wettability, being a measure for obtaining a good dyeing. Removal of the primary cell wall—especially the pectins—improves wax removal and ensures a more even dyeing. Further this improves the whiteness in the bleaching process. The main chemical used in scouring is sodium hydroxide in high concentrations, up to 70 g/kg cotton and at high temperatures, 80–95° C.; and c. Bleaching; normally the scouring is followed by a bleach using hydrogen peroxide as the oxidizing agent in order to obtain either a fully bleached (white) fabric or to ensure a clean shade of the dye.

A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme alpha-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

In the examples below it is shown that the scouring step can be carried out using the pectate lyase or pectate lyase preparation of the present invention a temperature of about 50° C.–80° C. and a pH of about 7–11, thus substituting or supplementing the highly causticizing agents. An optimized enzymatic process ensures a high pectin removal and full wettability.

Degradation or Modification of Plant Material

The enzyme or enzyme preparation according to the invention is preferably used as an agent for degradation or modification of plant cell walls or any pectin-containing material originating from plant cells walls due to the high plant cell wall degrading activity of the pectate lyase of the invention.

The pectate lyase of the present invention may be used alone or together with other enzymes like glucanases, pectinases and/or hemicellulases to improve the extraction of oil from oil-rich plant material, like soy-bean oil from soy-beans, olive-oil from olives or rapeseed-oil from rape-seed or sunflower oil from sunflower.

The pectate lyase of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions. The separation process may be performed by use of methods known in the art.

The pectate lyase of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearence of processed fruit or vegetables. The consistency and appearence has been shown to be a product of the actual combination of enzymes used for processing, i.e. the specificity of the enzymes with which the pectate lyase of the invention is combined. Examples include the production of clear juice e.g. from apples, pears or berries; cloud stable juice e.g. from apples, pears, berries, citrus or tomatoes; and purees e.g. from carrots and tomatoes.

The pectate lyase of the invention may be used in modifying the viscosity of plant cell wall derived material. For instance, the pectate lyase may be used to reduce the viscosity of feed which contain galactan and to promote processing of viscous galactan containing material. The viscosity reduction may be obtained by treating the galactan containing plant material with an enyme preparation of the invention under suitable conditions for full or partial degradation of the galactan containing material.

The pectate lyase can be used e.g. in combination with other enzymes for the removal of pectic substances from plant fibers. This removal is essential e.g. in the production of textile fibers or other cellulosic materials. For this purpose plant fiber material is treated with a suitable amount of the pectate lyase of the invention under suitable conditions for obtaining full or partial degradation of pectic substances associated with the plant fiber material.

Animal Feed Additive

Pectate lyases of the present invention may be used for modification of animal feed and may exert their effect either in vitro (by modifying components of the feed) or in vivo. the pectate lyase is particularly suited for addition to animal feed compositions containing high amounts of arabinogalactans or galactans, e.g. feed containing plant material from soy bean, rape seed, lupin etc. When added to the feed the pectate lyase significantly improves the in vivo breakdown of plant cell wall material, whereby a better utilization of the plant nutrients by the animal is achieved. Thereby, the growth rate and/or feed conversion ratio (i.e. the weight of ingested feed relative to weight gain) of the animal is improved. For example the indigestible galactan is degraded by pectate lyase, e.g. in combination with beta-galactosidase, to galactose or galactooligomers which are digestible by the animal and thus contribute to the available energy of the feed. Also, by the degradation of galactan the pectate lyase may improve the digestibility and uptake of non-carbohydrate feed constituents such as protein, fat and minerals.

For further description reference is made to PCT/DK96/00443 and a working example herein.

Wine and Juice Processing

The enzyme or enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

Determination of Catalytic Activity of Pectate Lyase

The Viscosity Assay APSU

APSU units: The APSU unit assay is a viscosity measurement using the substrate polygalacturonic acid with no added calcium.

The substrate 5% polygalacturonic acid sodium salt (Sigma P-1879) is solubilized in 0.1 M glycine buffer pH 10. The 4 ml substrate is preincubated for 5 min at 40° C. The enzyme is added (in a volume of 250 microliters) and mixed for 10 sec on a mixer at maximum speed, it is then incubated for 20 min at 40° C. For a standard curve double determination of a dilution of enzyme concentration in the range of 5 APSU/ml to above 100 APSU/ml with minimum of 4 concentrations between 10 and 60 APSU per ml.

The viscosity is measured using a MIVI 600 from the company Sofraser, 45700 Villemandeur, France. The viscosity is measured as mV after 10 sec.

For calculation of APSU units an enzyme standard dilution as described above was used for obtaining a standard curve:

| APSU/ml | mV |
|---|---|
| 0.00 | 300 |
| 4.00 | 276 |
| 9.00 | 249 |
| 14.00 | 227 |
| 19.00 | 206 |
| 24.00 | 188 |
| 34.00 | 177 |
| 49.00 | 163 |
| 99.00 | 168 |

The GrafPad Prism program, using a non-linear fit with a one phase exponential decay with a plateau, was used for calculations. The plateau plus span is the mV obtained without enzyme. The plateau is the mV of more than 100 APSU and the half reduction of viscosity in both examples was found to be 12 APSU units with a standard error of 1.5 APSU.

The Lyase Assay (at 235 nm)

For determination of the beta-elimination an assay measuring the increase in absorbance at 235 nm was carried out using the substrate 0.1% polygalacturonic acid sodium salt (Sigma P-1879) solubilised in 0.1 M Glycin buffer pH 10. For calculation of the catalytic rate an increase of 5.2 Absorbency at 235 units per min corresponds to formation of 1 $\mu$mol of unsaturated product (Nasuna and Starr (1966) J. Biol. Chem. Vol 241 page 5298–5306; and Bartling, Wegener and Olsen (1995) Microbiology Vol 141 page 873–881).

Steady state condition using a 0.5 ml cuvette with a 1 cm light path on a HP diode array spectrophotometer in a temperature controlled cuvette holder with continuous measurement of the absorbency at 235 nm. For steady state a linear increase for at least 200 sec was used for calculation of the rate. It was used for converted to formation $\mu$mol per min product.

Agar Assay

Pectate lyase activity can be measured by applying a test solution to 4 mm holes punched out in agar plates (such as, for example, LB agar), containing 0.7% w/v sodium polygalacturonate (Sigma P 1879). The plates are then incubated for 6 h at a particular temperature (such as, e.g., 75° C.). The plates are then soaked in either (i) 1 M CaCl$_2$ for 0.5 h or (ii) 1% mixed alkyl trimethylammonium Br (MTAB, Sigma M-7635) for 1 h. Both of these procedures cause the precipitation of polygalacturonate within the agar. Pectate lyase activity can be detected by the appearance of clear zones within a background of precipitated polygalacturonate. Sensitivity of the assay is calibrated using dilutions of a standard preparation of pectate lyase.

Endpoint Analysis—Transelimination at 235 nm for Pectate Lyases (high Calcium method: 1 mM Calcium in the final incubation mixture)

In this method, the substrate and enzyme is incubated for 20 min at 37° C. followed by measurement at 235 nm of the formation of double bounds. Finally, the rate of the degradation is calculated based on the molar extinction coefficient in terms of Trans Units.

Procedure:

Mixing of 0.5 ml enzyme dilution with 0,5 ml 2*substrate solution.

Substrate: Polygalactoronic acid from Sigma P-1879 lot 77H3784

Buffer 2×: 0.1 M glycine pH 10+2.0 mmol $CaCl_2$

Stop reagent: 0.02 M $H_3PO_4$

Temperature of incubation 37° C.

Reaction time 20 min.

Extinction coefficient of the transelimination 0.0052 micromol $cm^{-1}$.

Enzyme diluted in ion-free water to 0.5 to 5 APSU per ml.

Main value in duplicate 0.5 ml. The 2% w/v substrate in 2×buffer is mixed with 0.5 ml diluted enzyme. Both pre-incubated 5 min on water bath at 37° C. Incubate for 20 min. Stop using 5 ml stop reagent and mix. Blank mix enzyme and stop reagent first and then ad substrate all in the same volume.

| | |
|---|---|
| Enzyme | 0.5 ml |
| Substrate | 0.5 ml |
| Stop | 5 ml |
| Total volume | 6 ml |

Measure the absorbency at 235 nm in a 1 cm cuvette.

Calculate the formation of transelimination per min using the extinction coefficient of 0.0052 micro-mole $cm^{-1}$.

Calculation: [(main plus main)/2-Blank] 0.0052*6*2*Enzyme dilution/20 min/1000 ml=micro-mol per min.

Materials and Methods

Strains and Donor Organisms

*Bacillus licheniformis*, ATCC 14580, comprises the pectate lyase encoding DNA sequence presented in SEQ ID NO: 3.

*Bacillus agaradhaerens*, NCIMB 40482 or DSM 8721, comprises the pectate lyase encoding DNA sequence presented in SEQ ID NO: 1.

Bacillus sp. AAI12 comprises the pectate lyase encoding DNA sequence presented in SEQ ID NO: 5.

Bacillus sp. KJ59, DSM 12419, comprises the pectate lyase encoding DNA sequence presented in SEQ ID NO: 7.

Bacillus sp. I534 comprises the pectate lyase encoding DNA sequence presented in SEQ ID NO: 9.

*E. coli* DSM 12403 comprises the plasmid containing the pectate lyase encoding DNA sequence of the invention presented in SEQ ID NO: 5.

*E. coli* DSM 12404 comprises the plasmid containing the pectate lyase encoding DNA sequence of the invention presented in SEQ ID NO: 9.

*E. coli* DSM 11789 comprises the plasmid containing the pectate lyase encoding DNA sequence of the invention presented in SEQ ID NO: 3.

*E. coli* DSM 11788 comprises the plasmid containing the pectate lyase encoding DNA sequence of the invention presented in SEQ ID NO: 1.

*B. subtilis* PL2306. This strain is the *B. subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315–4321) disrupted in the transcriptional unit of the known *Bacillus subtilis* cellulase gene, resulting in cellulase negative cells. The disruption was performed essentially as described in Eds. A. L. Sonenshein, J. A. Hoch and Richard Losick (1993) *Bacillus subtilis* and other Gram-Positive Bacteria, American Society for microbiology, p. 618. Competent cells were prepared and transformed as described by Yasbin, R. E., Wilson, G. A. and Young, F. E. (1975) Transformation and transfection in lysogenic strains of *Bacillus subtilis:* evidence for selective induction of prophage in competent cells. J. Bacteriol, 121:296–304.

*E. coli:* SJ2 (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315–4321) Electrocompetent cells prepared and transformed using a Bio-Rad GenePulser™ as recommended by the manufacturer.

Plasmids pBK-CAMV (Stratagene Inc., La Jolla Calif.)

pSJ1678 (see WO 94/19454 Which is Hereby Incorporated by Reference in its Entirety)

pMOL944:

This plasmid is a pUB110 derivative essentially containing elements making the plasmid propagatable in *Bacillus subtilis*, kanamycin resistance gene and having a strong promoter and signal peptide cloned from the amyL gene of *B. licheniformis* ATCC14580. The signal peptide contains a SacII site making it convenient to clone the DNA encoding the mature part of a protein in-fusion with the signal peptide. This results in the expression of a pre-protein which is directed towards the exterior of the cell.

The plasmid was constructed by means of conventional genetic engineering techniques which are briefly described in the following. Construction of pMOL944:

The pUB110 plasmid (McKenzie, T. et al., 1986, Plasmid 15:93–103) was digested with the unique restriction enzyme NciI. A PCR fragment amplified from the amyL promoter encoded on the plasmid pDN1981 (P. L. Jørgensen et al., 1990, Gene, 96, p37–41.) was digested with NciI and inserted in the NciI digested pUB110 to give the plasmid pSJ2624.

The two PCR primers used have the following sequences:

```
# LWN5494 5'-GTCGCCGGGCGGCCGCTATCAATTGGTAACTGTATCTCAGC-3'       (SEQ ID NO:15)

# LWN5495 5'-GTCGCCCGGGAGCTCTGATCAGGTACCAAGCTTGTCGACCTGCAGAA   (SEQ ID NO:16)
        TGAGGCAGCAAGAAGAT-3'
```

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

LWN5938  5'-GTCGGCGGCCGCTGATCACGTACCAAGCTTGTCGACCTGCAGAATG  (SEQ ID NO:17)
          AGGCAGCAAGAAGAT-3'

LWN5939  5'-GTCGGAGCTCTATCAATTGGTAACTGTATCTCAGC-3'  (SEQ ID NO:18)

The plasmid pSJ2670 was digested with the restriction enzymes PstI and BclI and a PCR fragment amplified from a cloned DNA sequence encoding the alkaline amylase SP722 (disclosed in the International Patent Application published as WO 95/26397 which is hereby incorporated by reference in its entirety) was digested with PstI and BclI and inserted to give the plasmid pMOL944. The two primers used for PCR amplification have the following sequence:

LWN7864  5'-AACAGCTGATCACGACTGATCTTTTAGCTTGGCAC-3'  (SEQ ID NO:19)

LWN7901  5'-AACTGCAGCCGCGGCACATCATAATGGGACAAATGGG-3'  (SEQ ID NO:20)

The primer #LWN7901 inserts a SacII site in the plasmid.

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers (e.g. restriction endonucleases, ligases etc. are obtainable from New England Biolabs, Inc.).

Propagation of Donor Strains.

The strain *Bacillus licheniformis* ATCC 14580 was propagated in liquid medium 3 as specified by ATCC (American Type Culture Collection, USA). After 18 hours incubation at 37° C. and 300 rpm, the cells were harvested, and genomic DNA was isolated by the method described below.

*Bacillus agaradherens* NCIMB No. 40482, Bacillus sp. AAI12, Bacillus sp. KJ59, DSM 12419, and the Bacillus sp. I534 were all grown in TY with pH adjusted to approximately pH 9.7 by the addition of 50 ml of 1 M Sodium-Sesquicarbonate per 500 ml TY. After 24 hours incubation at 30° C. and 300 rpm, the cells were harvested, and genomic DNA was isolated by the method described below.

Genomic DNA Preparation

The Bacillus sp. strains described above as donor organisms were propagated in liquid media as described above. The cells were harvested, and genomic DNA was isolated by the method described by Pitcher et al. [Pitcher, D. G., Saunders, N. A., Owen, R. J; Rapid extraction of bacterial genomic DNA with guanidium thiocyanate; *Lett Appl Microbiol* 1989 8 151–156].

Creation of Bacteriophage Lambda Libraries from Alkali Tolerant Bacillus Species In order to enable us to screen for carbohydrases as plaques on indicator media, we selected LambdaZAP express cloning kit with BamHI digested and dephosphorylated arms from Stratagene. Bacillus DNA was isolated by the method of Pitcher et al., 1989). Isolated DNA was partially digested with Sau3A and size fractionated on a 1% DNA agarose gel. DNA was excised from the agarose gel between 2 and 6 Kb and purified using Qiaspin DNA fragment purification procedure (Qiagen GmBH). 100 ng of purified, fractionated DNA was ligated with 1 ug of BamHI dephosphorylated ZAPexpress vector arms (4 degrees overnight) Ligation reaction was packaged directly with GigaPackIII Gold according to the manufacturers instructions (Stratagene). Phage libraries were titered with XL1blue mrf-(Stratagene).

Creation of Plasmid Banks Derived from Primary Phage Libraries

Excision of phagmid banks from alkali Bacillus ZAPexpress libraries:

XL1-blue cells (Stratagene, La Jolla Calif.) were prepared and resuspended in 10 mM MgSO4 as recommended in the mass excission protocol in the Stratagene ZAPexpress handbook. 40,000 plaque forming units from each library were placed in Falcon 2059 tubes. Samples were incubated with 400 uls of XL1-blue cells and>$10^{10}$ pfus/ml EXassist M13 helper phage (Stratagene) at 37° C. for 15 minutes. Six mls of NZY broth was added to each tube and then the tubes were agitated at 37° C. for 2.5 hours. Samples were then heated at 65° C. for 20 minutes to kill *E. coli* cells and bacteriophage lambda; the phagmid being resistant to heating. Samples were spun at 3000 g to remove cellular debris and decanted into clean Falcon 2059 tubes. Single strand phagemid library samples were adjusted to 10% glycerol (cryopreservent) and titered according to the Stratagene protocol. Essentially, 10 uls of treated supernanant 1/10 diluted supernatant was used to infect 200 uls of XLOLR cells (cells in 10 mM MgSO4). Samples were placed in the 37° C. incubator 15 min. 50 uls of 5×NZY broth was added to the samples and they were agitated for 45 min at 37° C. 100 uls of sample were plated onto LB kanamycin plates and incubated overnight. After titer was obtained, for each library, 10,000 colony forming units was mixed with 400 uls XLOLR cells and incubated at room temperature for 20 minutes without agitation. XLOLR cells had been prepared as described in the Stratagene ZAPexpress manual (Stratagene inc., La Jolla Calif.). After 20 minutes, 200 uls of 5×NZY media, 3 mls of 1×NZY media was added to the samples. Samples were agitated at 200 rpm, 37° C. for 90 minutes. Glycerol was added to a final concentration of 10% and the cell were frozen in aliquots at −80° C. until further use.

Screening of the Libraries

Standard screening for pectinases on LB agar plates was performed as follows: Plasmid libraries in XLOLR *E. coli* cells were plated on LB kanamycin plates at a density of 5000 colony forming units per 140 mm diamater petri plates. Plates were incubated overnight at 37° C. then overlayed with 1% pectin DE 35% or DE 75% and 1% agarose. Plates were incubated overnight at 37° C. before being overlayed with 1% MTAB solution. After two hours the MTAB was poured off and the positive recombinant clones identified by a clearing zone around the colony. Positive isolates were reconfirmed by streaking on fresh LB media and testing again.

Media

TY (as described in Ausubel, F. M. et al. (eds.) "Current protocols in Molecular Biology". John Wiley and Sons, 1995).

LB agar (as described in Ausubel, F. M. et al. (eds.) "Current protocols in Molecular Biology". John Wiley and Sons, 1995).

LBPG is LB agar supplemented with 0.5% Glucose and 0.05 M potassium phosphate, pH 7.0

BPX media is described in EP 0 506 780 (WO 91/09129).

The following examples illustrate the invention.

EXAMPLE 1

Cloning, Expression, Purification and Characterization of a Pectate Lyase from Bacillus agaradhaerens Isolation of the DNA Sequence Encoding the Pectate Lyase of the Invention The DNA sequence comprising the DNA sequence shown in SEQ ID NO: 1 and encoding the pectate lyase of the invention can be obtained from the deposited organism E. coli, DSM 11788, by extraction of plasmid DNA by methods known in the art (Sambrook et al. (1989) Molecular cloning: A laboratory manual, Cold Spring Harbor Lab., Cold Spring Harbor, N.Y.).

Genomic Library Construction of Bacillus agaradhaerens

Genomic DNA of Bacillus agaradhaerens NCIMB 40482 was partially digested with restriction enzyme Sau3A, and size-fractionated by electrophoresis on a 0.7% agarose gel. Fragments between 2 and 7 kb in size were isolated by electrophoresis onto DEAE-cellulose paper (Dretzen, G., Bellard, M., Sassone-Corsi, P., Chambon, P. (1981) A reliable method for the recovery of DNA fragments from agarose and acrylamide gels. Anal. Biochem., 112, 295–298).

Isolated DNA fragments were ligated to BamHI digested pSJ1678 plasmid DNA, and the ligation mixture was used to transform E. coli SJ2. Transformed cells from the Genomic library of Bacillus agaradhaerens NCIMB 40482 were plated on LB-agar plates containing 10 μg/ml of Chloramphenicol and 0.7%, sodium polygalacturonate (SIGMA P-1879). The plated cells were incubated 16 hours at 37° C. The colonies were replica plated onto fresh LB-agar plates containing 10 μg/ml of Chloramphenicol and 0.7%, sodium polygalacturonate (SIGMA P-1879) these plates were incubated 8 hours at 37° C. The original master plates were flooded with 5 ml 1 M $CaCl_2$, after 5 to 30 min distinct cloudy halos appeared around putative Sodium Polygalacturonate degrading clones. The corresponding masterplate clones were picked for further characterization. These clones were further characterized by preparing plasmid DNA from overnight 30° C. liquid TY cultures of the E. coli clones and preparing plasmid DNA using Qiagen Qiaspin Prep Kit as according to manufacturer (Qiagen, Germany).

The pectate lyase positive clone of Bacillus agaradhaerens NCIMB 40482 Gene library was deposited as DSM 11788. After primer walking on the plasmid of the E. coli DSM 11788 the SEQ ID NO: 1 of the pectate lyase encoding DNA from Bacillus agaradhaerens NCIMB No. 40482 was identified.

Identification of Positive Clones by Activity

After incubation on plates the colonies were replica plated onto a set of LB+6 CAM agar plates and then further incubated at 37° C. for approx. 20 hours. An overlayer containing 1% HSB agarose, 0.7% polygalacturonic acid sodium salt in an appropriate buffer was poured onto the replica plates and incubated for approx. 20 hours at 40° C. After precipitation with MTA3 pectate lyase positive colonies were identified by the appearance of clear Halos at positions where pectate lyase positive clones were present.

Cells from pectate lyase positive colonies were spread for single colony isolation on agar, and a pectate lyase producing single colony was selected for each of the pectate lyase-producing colonies identified.

Characterization of Positive Clones

From the restreaking plates the pectinase positive clones were obtained as single colonies, and plasmids were extracted using Qiagen Plasmid Prep as indicated by the manufacturer (Qiagen, Germany). Phenotypes were confirmed by retransformation of E. coli SJ2, and plasmids characterized by restriction digests.

Expression in Bacillus subtilis of the Cloned Gene Encoding a Pectate Lyase

Plasmid prep of the E. coli, DSM 11788, containing the cloned gene on pSJ1678 (an E. coli/B. subtilis shuttle vector), was used to transform B. subtilis PL2306. Competent cells were prepared and transformed as described by Yasbin et al. [Yasbin R E, Wilson G A & Young F E; Transformation and transfection in lysogenic strains of Bacillus subtilis: evidence for selective induction of prophage in competent cells; J. Bacteriol 1975 121 296–304].

Isolation and Test of Bacillus subtilis Transformants

The transformed cells were plated on LB agar plates containing 6 mg/ml Chloramphenicol, 0.4% glucose, 10 mM $KH_2PO_4$, and incubated at 37° C. for 18 hours. Pectate lyase positive colonies were identified as done above with E. coli.

Each of the positive transformants was inoculated in 10 ml TY-medium containing 6 mg/ml Chloramphenicol. After 1 day of incubation at 37° C. and shaking at 250 rpm, 50 microliters supernatant was removed. The pectate lyase activity was identified by adding 10 microliters supernatant to holes punched in the agar of LB agar plates containing 0.7% sodium polypectate (Sigma, US).

After 16 hours of incubation at 37° C., plates were soaked in 1 M $CaCl_2$ for 5 to 30 min. Distinct cloudy halos appeared where supernatant contained pectate lyase from a clone expressing the pectate lyase. One such clone was called MB464.

The cells were removed by centrifugation and the remaining supernatant was used as source for purifying the pectate lyase.

Purification and Characterization

The B. subtilis transformant obtained as described above was incubated in 100 ml of TY containing 6 mg/ml Chloramphenicol. After overnight incubation at 37° C. and stirring at 250 rpm, the culture was used as inoculum in 1 l shake flasks containing 100 ml of Complex Growth Medium (U.S. Pat. No. 5,371,198, example 1 which is hereby incorporated by reference).

1 ml of culture was the inoculum volume, the cultures were incubated 37° C. and shaked at 250 rpm for 4 days.

The fermentation medium was adjusted to pH 7.5 with NaOH and flocculated using cationic flocculation agent C521 (10% solution) and 0.1% solution of anionic agent A130: To 6500 ml of fermentation medium was added 306 ml of C521 (10%) simultaneous with 608 ml of A130 under stirring at room temperature. The flocculated material was separated by centrifugation using a Sorval RC 3B centrifuge at 10,000 rpm for 30 minutes. The supernatant was clarified using Whatman glass filter number F. In total was obtained 7200 ml of clear solution.

The liquid was concentrated into 2 portions of 500 ml and 840 ml, respectively, using filtron ultrafiltration with a MW cut off of 10 kDa.

The pH was adjusted to 5.3 using acetic acid, and the concentrate was applied to a 200 ml S-Sepharose column equilibrated with 50 mM sodium acetate buffer, pH 5.3. The pectate lyase of the invention (*B. agaradhaerens*) eluted using a linear gradient of 2 l with 0.5 M NaCl as final concentration. Pectate lyase from *Bacillus subtilis* will also bind to Sepharose at this pH but it has a higher pI (7.6 versus 6.0). So the cloned pectate lyase of the invention elutes first, fractions were analyzed for APSU units and for reaction with antiserum raised against *Bacillus subtilis* pectate lyase.

The *Bacillus agaradhaerens* pectate lyase was concentrated using an Amicon ultrafiltration cell with a GR61 membrane with a cut off of 20 kDa.

A total of 90,000 APSU units was obtained. This sample was free of protease and of the *Bacillus subtilis* pectate lyase determined using antiserum raised against *Bacillus subtilis* pectate lyase.

The pectate lyase enzyme of the invention could be easily seen in SDS-PAGE as a band with a MW of 36 kDa. After electroblotting of this band the N-terminal was determined as:

Ser-Asn-Gly-Pro-Gln-Gly-Tyr-Ala-Ser-Met-Asn-Gly-Gly-Thr

This is in agreement with the amino acid sequence shown in SEQ ID NO: 2 deduced from the DNA sequence shown in SEQ ID NO: 1 with a 33 amino acid pro sequence. The calculated MW from the deduced sequence was 36 kDa and the calculated pI was 6. The molar extinction coefficient at 280 nm was 48,930.

The beta-transelimination activity (using the lyase assay at 235 nm) at different pH values was determined as steady state kinetic at 40° C. The relative rate is calculated as percentage of the optimum activity, the following result was obtained:

| PH | % activity |
| --- | --- |
| 6.5 | 0 |
| 7 | 5 |
| 7.5 | 8 |
| 8 | 21 |
| 8.5 | 32 |
| 9 | 38 |
| 9.5 | 39 |
| 10 | 52 |
| 10.5 | 47 |
| 11 | 100 |
| 11.2 | 66 |
| 11.5 | 3 |

The pH profile was determined using the following buffers:

| pH 6.0: | Na-MES | 0.1M |
| --- | --- | --- |
| pH 6.5, 7.0 and 7.5: | Na-MOPS | 0.1M |
| pH 8.0 & 8.5: | Tris | 0.1M |
| pH 9.0, 9.5, 10.0 and 10.5: | Na-glycine | 0.1M |
| pH 11–11.5: | Na-Carbonate | 0.1M |

MES is 2[N-Morpholino]ethanesulfonicAcid (Sigma, No. M-8250)

MOPS is 3-[N-Morpholino]propanesulfonic Acid (SIGMA, No. M-1254).

Tris (Merck No. 1.08382).

Glycine (Merck).

Sodium carbonate (Merck No. 6392).

Correspondingly, the relative activity at different temperatures (at pH 10) was found:

| temp.° C. | % activity |
| --- | --- |
| 40 | 69 |
| 50 | 100 |
| 55 | 97 |
| 60 | 68 |
| 65 | 71 |

Subcloning in *B. subtilis*

The pectate lyase encoding DNA sequence of the invention (SEQ ID NO: 1) was PCR amplified using the PCR primer set consisting of these two oligo nucleotides:

```
Pecl.B.aga.uppper.SacII
5'-CTG CAG CCG CGG CAG CTG CTT CAA ATC AGC CAA CTT C-3'  (SEQ ID NO: 21)

Pecl.B.aga.lower.NotI
5'-GCG TTG AGA CGC GCG GCC GCT TTA CTC TGC ACA CAG GCA GAG C-3'  (SEQ ID NO: 22).
```

Restriction sites SacII and NotI are underlined.

Chromosomal DNA isolated from *B. agaradhaerens* NCIMB 40482 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 µM of each dNTP, 2.5 units of AmpliTaq polymerase (Perkin-Elmer, Cetus, USA) and 100 pmol of each primer.

The PCR reaction was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five µl aliquots of the amplification product was analyzed by electrophoresis in 0.7% agarose gels (NuSieve, FMC). The appearance of a DNA fragment size 1.0 kb indicated proper amplification of the gene segment.

Subcloning of PCR Fragment

Forty five microliters aliquots of the PCR products generated as described above were purified using QIAquick PCR purification kit (Qiagen, USA) according to the manufacturer's instructions. The purified DNA was eluted in 50 microliters of 10 mM Tris-HCl, pH 8.5.

5 micrograms of pMOL944 and twenty five microliters of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 micrograms of each DNA fragment, 1 U of T4 DNA ligase and T4 ligase buffer (Boehringer Mannheim, Germany).

The ligation mixture was used to transform competent *B. subtilis* PL2306. The transformed cells were plated onto LBPG-10 micrograms/ml of Kanamycin plates. After 18 hours incubation at 37° C. several clones were restreaked on fresh agar plates and also grown in liquid TY cultures with 10 micrograms/ml kanamycin and incubated overnight at 37° C. Next day 1 ml of cells were used to isolate plasmid from the cells using the Qiaprep Spin Plasmid Miniprep Kit #27106 according to the manufacturers recommendations for B. subtilis plasmid preparations. This plasmid DNA was used as template for DNA sequencing.

One clone containing the pectate lyase gene was kept, this clone was termed MB504.

The DNA corresponding to the mature part of the pectate lyase was characterized by DNA sequencing by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984) Nucleic Acids Res. 12, 387–395. The cloned DNA sequence was expressed in B. subtilis and the protein that appeared in the supernatant corresponded to the mature protein represented in SEQ ID NO: 2 mature protein.

Purification and Characterization 5000 ml of culture fluid of the B. subtilis transformant obtained as described above (MB504) was flocculated using 125 ml 10% C521 (cation) and 200 ml 0.1% A130 (anion) at pH 7.5, followed by centrifugation and filtration. The clear supernatant was concentrated on a filtron UF membrane with a cut off of 10 kDa to final volume of 720 ml.

For obtaining a highly pure enzyme 40 ml was adjusted to pH 8.0 using NaOH and then applied to 50 ml Q-Sepharose column equilibrated with 25 mM Tris HCl pH 8.0. The pectate lyase eluted from the column using a NaCl gradient. The eluted pectate lyase (total 150 ml) was concentrated using an Amicon ultrafiltration cell with a membrane with a cut off of 10 kDa. The concentrate was applied to a Superdex 200 column and a pure pectate lyase with a MW of 38 kDa with an isoelectric point around 6.1 was obtained.

The pure enzyme was dialysed against EDTA at pH 8.0 (20 mM tris pH 8.0), and at pH 10 (20 mM Glycine pH 10) and was analyzed in Circular dichroism: No differences were seen in the spectra with and with out EDTA.

Differential Scanning Calorimetry DSC of the 4 samples showed that the enzyme was most stable at pH 8.0 with a melting temperature around 61° C. in Tris pH 8.0 and 62° C. after dialysis against EDTA. At pH 10 the enzyme melted at 59° C. with and without EDTA.

The catalytic activity is inhibited by the presence of EDTA during incubation with substrate but the enzyme dialysed against EDTA was still active if EDTA was omitted during incubation with substrate. Divalent cations like Fe++, Li++, Mg++, Cu++, Mn++ have no effect on the catalytic activity.

Activity in Detergents

Using commercial detergents instead of buffer and incubating for 20 minutes at 40° C. with Polygalacturonic acid sodium salt (Sigma P-1879) followed by determination of the reducing sugars, the enzyme was active in the commercially available European powder laundry detergent Ariel Futur™ with 37% relative activity, in the commercially available US powder laundry detergent Tide™ with 58% relative activity and in the commercially available US liquid detergent Tide™ with 37% relative activity to the activity measured in Glycine buffer. The detergent concentration was equal to the concentration recommended on the detergent packages for household use, and the used water tap water had 18 degrees German hardness (European detergent/European conditions) and 9 degrees German hardness (US detergents/US conditions).

Immunological Properties

At the Danish company DAKO, rabbit polyclonal monospecific serum was raised against the highly purified pectate lyase prepared as described above using conventional techniques. The serum formed a nice single precipitate in agarose gels with the B. agarahaerens pectate lyase of the invention.

EXAMPLE 2

Cloning, Expression, Purification and Characterization of a Pectate Lyase from Bacillus licheniformis Genomic library construction of Bacillus licheniformis, ATCC 14580, was carried out as described in example 1 for B. agaradhaerens. The pectate lyase positive clone of Bacillus licheniformis ATCC 14580 Gene library was deposited as DSM 11789. After primer walking on the plasmid of the E. coli DSM 11789 the SEQ ID NO: 3 of the pectate lyase encoding DNA from Bacillus licheniformis ATCC 14580 was identified.

Subcloning in Bacillus subtilis

The pectate lyase (represented by amino acid sequence SEQ ID NO: 4) encoding DNA sequence of the invention was PCR amplified using the PCR primer set consisting of these two oligo nucleotides:

```
Pecl.B.lich.uppper.SacII
5'-CTA ACT GCA GCC GCG GCA GCT TCT GCC TTA AAC TCG GGC-3'  (SEQ ID NO: 23)

Pecl.B.lich.lower.NotI
5'-GCG TTG AGA CGC GCG GCC GCT GAA TGC CCC GGA CGT TTC ACC-3'  (SEQ ID NO: 24)
```

Restriction sites SacII and NotII are underlined.

Chromosomal DNA isolated from B. licheniformis ATCC 14580 as described above was used as template in a PCR reaction in a PCR reaction carried out as described in example 1. The appearance of a DNA fragment size 1.0 kb indicated proper amplification of the gene segment.

Subcloning of PCR fragment was carried out as described in example 1 except that the purified PCR fragment was digested with SacII and NotII. One clone containing the pectate lyase gene was kept, this clone was termed MB541. The DNA corresponding to the mature part of the pectate lyase was characterized by DNA sequencing by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984) Nucleic Acids Res. 12, 387–395. The cloned DNA sequence was expressed in B. subtilis and the protein that appeared in the supernatant corresponded to the mature protein represented in SEQ ID NO: 4.

Purification

MB541 was grown in 25×200 ml BPX media with 10 micrograms/ml of Kanamycin in 500 ml two baffled shakeflasks for 5 days at 37° C. at 300 rpm, whereby 3500 ml of culture broth was obtained. The pH was adjusted to 5.0 using acetic acid and 100 ml of cationic agent (C521) and 200 ml of anionic agent (A130) was added during agitation for flocculation. The flocculated material was separated by centrifugation using a Sorval RC 3B centrifuge at 10000 rpm for 30 min at 6° C. The resulting supernatant contained 370 APSU per ml in a total volume of 3600 ml.

The supernatant was clarified using Whatman glass filters GF/D and C and finally concentrated on a filtron UF membrane with a cut off of 10 kDa. The total volume of 2000 ml was adjusted to pH 8.5. 50 gram of DEAE A-50 Sephadex (Pharmacia) was swelled in 2000 ml 50 MM Tris pH 8.5. Excess buffer was discarded and the clear concentrated enzyme solution was mixed with the slurry for 15 min. The enzyme was separated from the ion-exchange material by suction on a Buchner funnel. The resulting solution was concentrated on a filtron with a cut off of 10 kDa to a final volume of 800 ml.

For obtaining a highly purified pectate lyase a final step using S-sepharose cation-exchange chromatography was carried out. 50 ml of the solution of 950 APSU per ml (see above) was adjusted to pH 5.0 using acetic acid. It was applied to a 50 ml column containing S-Sepharose (Pharmacia) equilibrated with a buffer of 50 mmol sodium acetate pH 5.0. The pectate lyase bound and was eluted using a gradient of 0.5 M sodium chloride.

Characterization

The pure enzyme gave a single band in SDS-PAGE of 35 kDa and an isoelectric point of around 6.1.

The protein concentration was determined using a molar extinction coefficient of 57750 (based on the amino acid composition deducted from the sequence).

Using the assay of detection the formation of cleavage by the formation of a double bound which can be measured at 235 nm the following data were obtained 1. (conditions: pH 10; glycine buffer; no calcium; polygalacturonic acid Sigma P-1879 as substrate): 1 μmol per min per mg.
2. (conditions: pH 10; glycine buffer; no calcium; DE 35 (35% esterified pectin) as substrate): 4 μmol per min per mg.

The pure enzyme was dialysed against EDTA at pH 8.0 (20 mM tris pH 8.0, and at pH 10 (20 mM Glycine pH 10) and the enzyme analyzed in Circular dichroism, no differences was seen in the spectra with and with out EDTA.

Differential Scanning Calorimetry DSC of the 4 samples showed that the enzyme was most stable at pH 8.0 with a melting temperature around 70° C. in Tris pH 8.0 and 75° C. after dialysis against EDTA. At pH 10 the enzyme melted at 55° C. with and without EDTA.

The catalytic activity of the pectate lyase is inhibited by the presence of EDTA during incubation with substrate but the enzyme dialysed against EDTA was still active if EDTA was omitted during incubation with substrate. Divalent cation like Fe++, Li++, Mg++, Cu++, Mn++ has no effect on the catalytic activity.

The beta-transelimination activity (using the lyase assay at 235 nm) at different pH values was determined as steady state kinetic at 40° C. using the following buffers:

| pH 6.0: | Na-MES | 0.1M |
| pH 6.5, 7.0 & 7.5: | Na-MOPS | 0.1M |
| pH 8.0 & 8.5: | Tris | 0.1M |
| pH 9.0, 9.5, 10.0 & 10.5: | Na-glycine | 0.1M |
| pH 11–11.5: | Na-Carbonate | 0.1M |

MES: From SIGMA number M-8250 (2[N-Morpholino] ethane sulfonic acid).

MOPS: From SIGMA number M-1254 (3-[N-Morpholino] propane sulfonic acid).

Tris: From Merck No. 1.08382

Glycine from MERCK and sodium carbonate from Merck No. 6392.

The relative activity (rate) is calculated as percentage of the optimum activity, the following result was obtained:

| PH | % activity |
| --- | --- |
| 6.5 | 1 |
| 7 | 5 |
| 7.5 | 4 |
| 8 | 4 |
| 8.5 | 4 |
| 9 | 6 |
| 9.5 | 23 |
| 10 | 100 |
| 10.5 | n.d. |
| 11 | 52 |
| 11.2 | 0 |

Correspondingly, the relative activity at different temperatures (at pH 10) was found:

| temp.° C. | % activity |
| --- | --- |
| 40 | 65 |
| 50 | 87 |
| 55 | 87 |
| 60 | 100 |
| 65 | 90 |

Activity in detergents: Using commercial detergents instead of on for 20 min. at 40° C. with Polygalacturonic acid sodium salt (sigma P-1879) followed by determination of the reducing sugars, the enzyme was active in European commercial powder detergent Ariel Futur with 44% relative activity, US Tide comercial powder with 51% relative activity and in US Tide commercial liquid detergent with 30% relative activity to the activity measured in Glycine buffer. The detergent concentration as the one recommended for use and the water tap water with 18 degrees German hardness under European conditions and 9 degrees under US conditions.

Immunological properties: At the Danish company DAKO, rabbit polyclonal monospecific serum was raised against the highly purified pectate lysae using conventional techniques. The serum formed a nice single precipitate in agarose gels with the pectate lyase of the invention and only one precipitation arch against *Bacillus licheniformis* products like Pulpzyme HC batch no. CKF0054 or batch no. CKN00009 from Novo Nordisk A/S.

EXAMPLE 3

Cloning, Expression, Purification and Characterization of a Pectate Lyase from Bacillus sp. KJ59, DSM 12419

Subcloning in *B. subtilis* of the DNA sequence encoding the mature part of the pectate lyase (SEQ ID NO: 7).

Using the exact same procedure as decribed in example 1, the DNA sequence encoding the mature part of the pectate lyase encoded in SEQ ID NO: 7 was cloned and expressed in the pMOL944/PL2306 expression system. The only difference was that the following two PCR primers were used and genomic DNA isolated from Bacillus sp. KJ59, DSM12419, was used instead:

145375
5'-CAT TCT GCA GCC GCG GCA AAT ACG CCA AAT TTC AAC TTA CAA G-3' (SEQ ID NO: 25)
145376
5'-CAG CAG TAG CGG CCG CTT ACG GTT GGA TGA CAC CAA CTC-3' (SEQ ID NO: 26)

The resulting *B. subtilis* clone expressing the pectate lyase was termed MB888. The cloned DNA sequence was expressed in *B. subtilis* and the protein that appeared in the supernatant corresponded to the mature protein represented in SEQ ID NO: 8 mature protein.

Purification

*Bacillus subtilis* transformed with this plasmid (MB888) was grown PS medium containing Kanamycin.

Flocculation was done using cationic flocculation agent C521 (10% solution) and 0.1% solution of anionic agent A130: To 2000 ml of fermentation medium was added 2000 ml ion free water and it had pH 6.0 then 80 ml of C521 (10%) simultaneously with 40 ml of A130 was added under stirring at room temperature. The flocculated material was separated by centrifugation using a Sorval RC 3B centrifuge at 10,000 rpm for 30 minutes. The supernatant was clarified using Whatman glass filter number F. In total was obtained 40000 ml of clear solution containing 204,000 Trans Units.

The liquid was concentrated into 500 ml using filtron ultrafiltration with a MW cut off of 10 kDa. The Concentrate was treated with 5 gram of DEAE A-50 Sephadex equilibrated in 25 mM Tris pH 8.0 for 30 minutes and the pectate lyase did not bind and was filtrated free of the ionexchange material. The filtrate was adjusted to pH 5.0 using HCl and applied to S-Sepharose column equilibrated with 25 mM Sodium acetate pH 5.0. The pectate lyase bound and was eluted as a pure protein using a NaCl gradient.

Characterization

The pure enzyme has a MW of 36 kDa and a pI of 8.98.
The temperature optimum at pH 10 is about 65° C.
The relative activity is higher than 50% active at 40° C. between pH 9 and 11.
The pectate lyase has a melting temperature of 74° C. measured using DSC in 0.1 M sodium acetate pH 6.0.

EXAMPLE 4

Cloning, Expression, Purification and Characterization of a Pectate Lyase from Bacillus sp. I534

Subcloning in *B. subtilis* of the DNA Sequence Encoding the Mature Part of the Pectate Lyase (SEQ ID NO: 9).

Using the exact same procedure as descibed above, the DNA sequence encoding the mature part of the pectate lyase (SEQ ID NO: 9) was cloned and expressed in the pMOL944/PL2306 expression system. The only difference was that the following two PCR primers were used and genomic DNA isolated from Bacillus sp. I534 was used instead:

136558
5'-CCT GCA GCC GCG GCA AAA GGT GAA AGC GAT TCC ACT ATG-3' (SEQ ID NO: 27)
136559
5'-GTT GAG AAA AGC GGC CGC AAC GGA CAC TCG GCT TTA GAG-3' (SEQ ID NO: 28)

The resulting *B. subtilis* clone expressing the pectate lyase was termed MB746. The cloned DNA sequence was expressed in *B. subtilis* and the protein that appeared in the supernatant corresponded to the mature protein represented in SEQ ID NO: 10 mature protein.

Purification

*Bacillus subtilis* transformed with this plasmid (MB746) was grown in PS medium containing Kanamycin.

Flocculation was done using cationic flocculation agent C521 (10% solution) and 0.1% solution of anionic agent A130: To 3700 ml of fermentation medium was adjusted to pH 5.5 using HCl and then added 37 ml of C521 (10%) simultaneous with 75 ml of A130 under stirring at room temperature. The flocculated material was separated by centrifugation using a Sorval RC 3B centrifuge at 10,000 rpm for 30 minutes. The supernatant was clarified using Whatman glass filter number F. In total was obtained 40000 ml of clear solution containing 1,044,000 Trans Units.

The liquid was concentrated into 550 ml using filtron ultrafiltration with a MW cut off of 10 kDa. This product was used for application trials after stabilization using 50% MPG (batch #9831).

Highly purified enzyme was obtained using Anionic chromatography (HPQ column at pH 8.0 using a 25 mM tris buffer); the enzyme eluted using a NaCl gradient, the final purification step was a size chromatography on a Superdex 200 column run in a 0.1 M Sodium acetate buffer.

Characterization

The pure enzyme has a MW of 35 kDa and an isoelectrial point (pI) of 6.2.
The temperature optimum at pH 10 is above 70° C.
The relative activity is more than 50% between pH 9 and 11 at a temperature of 40° C.
The N-terminal of the purified pectate lyase has the amino acid sequence KGESDSTMNA starting at position 25 of the amino acid sequence SEQ ID NO: 10.

EXAMPLE 5

Cloning, Expression, Purification and Characterization of a Pectate Lyase from Bacillus sp. AAI12

Subcloning in *B. subtilis* of the DNA Sequence Encoding the Mature Part of the Pectate Lyase (SEQ ID NO: 5)

Using the exact same procedure as described in example 1, the DNA sequence encoding the mature part of the pectate lyase (SEQ ID NO: 5) was cloned and expressed in the pMOL944/PL2306 expression system. The only difference was that the following two PCR primers were used and genomic DNA isolated from Bacillus sp. AAI12 was used instead:

80501D1C12
5'-CAT TCT GCA GCC GCG GCA GCA TCA TTT CAG TCT AAT AAA AAT TAT C-3' (SEQ ID NO: 29)
80501D1B12
5'-GAC GAC GTA CAA GCG GCC GCG CTA CTG TAC AAC CCC TAC ACC-3' (SEQ ID NO: 30)

The resulting *B. subtilis* clone expressing the pectate lyase was termed MB644. The cloned DNA sequence was expressed in *B. subtilis* and the protein that appeared in the supernatant corresponded to the mature protein represented in SEQ ID NO: 6 mature protein.

Purification and Characterization

*Bacillus subtilis* transformed with this plasmid (MB644) was grown in PS medium containing kanamycin.

It was found that this enzyme contains 3 lectin binding domains at the N-terminal.

EXAMPLE 6

Pectate Lyase Treatment of Cellulosic Material:
Effect of Temperature on Pectin Removal and Wettability A 100% cotton woven twill fabric, desized Test Fabric #428U, representing a typical cellulosic material, was treated with an aqueous enzyme solution comprising the *B. licheniformis* pectate lyase of example 2, dosed at 9 APSU/g fabric at pH 9 and at a 15:1 liquor ratio. Treatment time was 2 hours and temperature varied between 35–75° C. The fabric was rinsed well after the enzyme treatment, dried and then dyed with Ruthenium Red. The dye uptake was measured spectrophotometrically and is a measure of the residual pectin on the fiber. The percentage of residual pectin was calculated using the dye uptake of the starting material as 100% residual pectin and that of fully chemically scoured and bleached fabric as 0%. Results are shown in Table 1. Further, the wettability (drop test—measuring the time in seconds for a drop of water to become absorbed by the fabric) was measured and compared to a no enzyme control. Results are shown in Table 2.

TABLE 1

| | (% residual pectin) | | | | |
|---|---|---|---|---|---|
| Temp., °C. | 35 | 45 | 55 | 65 | 75 |
| no enzyme | 100 | 100 | 93 | 90 | 85 |
| enzyme | 52 | 40 | 32 | 28 | 26 | an alkaline scouring leaves typically 20–25% residual pectin

TABLE 2

| Temp., °C. | 35 | 45 | 55 | 65 | 75 |
|---|---|---|---|---|---|
| No enzyme | 32 | 29 | 29 | 12 | 11 |
| enzyme | 15 | 10 | 7 | 5 | 3 | wettability target is typically <5 seconds

The beneficial effect of increasing temperature is clearly seen on both responses.

EXAMPLE 7

Pectate Lyase Treatment of Cellulosic Material:
Effect of pH on Pectin Removal

A 100% cotton woven twill fabric, desized Test Fabric #428U, representing a typical cellulosic material, was treated with an aqueous enzyme solution comprising the *B. licheniformis* pectate lyase of example 2, dosed at 9 APSU/g fabric at a 15:1 liquor ratio. Treatment time was 2 hours and the temperature 55° C. pH was varied between 8–11. The fabric was rinsed well after the enzyme treatment, dried and then dyed with Ruthenium Red. The dye uptake is measured spectrophotometrically and is a measure of the residual pectin on the fiber. The percentage of residual pectin was calculated using the dye uptake of the starting material as 100% residual pectin and that of fully chemically scoured and bleached fabric as 0%. The results are shown in Table 3:

TABLE 3

| pH | 8 | 9 | 10 | 10.5 | 11 |
|---|---|---|---|---|---|
| % residual pectin | 35 | 32 | 30 | 48 | 61 |

The pH optimum is found to be at app. 9.5, but a good activity is demonstrated in a very broad alkaline interval.

EXAMPLE 8

Use of the Enzyme of the Invention in Detergents

The purified enzyme obtained as described in example 2 (batch 9751) showed improved cleaning performance when tested at a level of 1 ppm in a miniwash test using a conventional commercial liquid detergent. The test was carried out under conventional North American wash conditions.

EXAMPLE 9

Effects of Carbohydrases on Banana Stained Cotton Textile
Method

Three bananas were mashed and homogenised in a Ultra Turrax with 40 ml of water. Style 400 cotton (Testfabrics, Inc.) was soaked in the solution, squeezed between two rolls and dried overnight.

The stained cotton textile was washed in the commercial liquid detergent brand Ariel Futur Liquid under European wash conditions, with an addition of 0.1 ppm, 0.2 ppm, 1 ppm and 10 ppm, respectively, of the pectate lyase of example 2 to the detergent liquid and an addition of 10 ppm of the pectate lyase of example 1. The test was repeated.
Results Ariel liquid: % removal of the banana stains (100% is total removal of stain)

| | Test A | Test B |
|---|---|---|
| No enzyme | 26% | 32% |
| 10 ppm enzyme, ex 2 | 59% | 58% |
| 1 ppm enzyme, ex 2 | 47% | 48% |
| 0.1 ppm enzyme, ex 2 | 35% | 34% |
| 10 ppm enzyme, ex 1 | — | 45% |

EXAMPLE 10

Construction and Expression of Fusion Protein Between Pectate Lyase and CBD

The CBD encoding DNA sequence of the CipB gene from *Clostridium thermocellum* strain YS (Poole D M; Morag E; Lamed R; Bayer EA; Hazlewood G P; Gilbert H J (1992) Identification of the cellulose-binding domain of the cellulosome subunit S1 from *Clostridium thermocellum* YS, Fems Microbiology Letters Vol. 78, No. 2–3 pp. 181–186 was PCR amplified using the PCR primer set consisting of the following two oligo nucleotides:

CIPCBD.upper.PECL.SalI

5'-CGA CAA TGT CGA CAA TGT AAA ATC AAT CGT CAA GCA AAA TGC CGG AGT CGG CAA AAT CCA GCG CAG ACC GCC AAC ACC GAC CCC GAC TTC ACC GCC AAG CGC AAA TAC ACC GGT ATC AGG CAA TTT G-3' (SEQ ID NO: 31)

CIPCBD.lower.NotI

5'-GCG TTG AGA CGC GCG GCC GCT ATA CCA CAC TGC CAC CGG GTT CTT TAC-3' (SEQ ID NO: 32).

Restriction sites SalI and NotI are underlined.

Chromosomal DNA encoding the CBD can be obtained as described in Poole D M; Morag E; Lamed R; Bayer E A; Hazlewood G P Gilbert H J (1992) Identification of the cellulose-binding domain of the cellulosome subunit S1 from *Clostridium thermocellum* YS, Fems Microbiology Letters Vol. 78, No. 2–3 pp. 181–186. A DNA sample encoding the CBD was used as template in a PCR reaction carried out as described in example 1. The appearance of a DNA fragment approximate size of 0.5 kb indicated proper amplification of the gene segment.
Subcloning of PCR Fragment The subcloning was carried out as described in example 1 except that the purified PCR fragment was digested with SalI and NotI. Several clones were analyzed by isolating plasmid DNA from overnight culture broth.

One such positive clone was restreaked several times on agar plates as used above, this clone was called MB914. The clone MB914 was grown overnight in TY-10 micrograms/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations. This DNA was DNA sequenced and revealed the DNA sequence corresponding to the fusion protein of: Pectate lyase-linker-cbd as represented in SEQ ID NO: 11 and in the sequence of SEQ ID NO: 12.

Expression and Detection of Pectate-lyase-cbd Fusion Protein

MB914 was incubated for 20 hours in TY-medium at 37° C. and 250 rpm. 1 ml of cell-free supernatant was mixed with 200 microliters of 10% Avicel (Merck, Darmstadt, Germany) in Millipore $H_2O$. The mixture was left for ½ hour incubation at 0° C. After this binding of Pectatelyase-Linker-CBD fusion protein to Avicel the Avicel with bound protein was spun 5 min at 5000 g. The pellet was resuspended in 100 µl of SDS-page buffer, boiled at 95° C. for 5 min, spun at 5000 g for 5 min and 25 microliters was loaded on a 4–20% Laemmli Tris-Glycine, SDS-PAGE NOVEX gel (Novex, USA). The samples were electrophoresed in an Xcell™ Mini-Cell (NOVEX, USA) as recommended by the manufacturer, all subsequent handling of gels including staining with comassie, destaining and drying were performed as described by the manufacturer.

The appearance of a protein band of approx. 55 kDa, indicated expression in *B. subtilis* of the pectate lyase-Linker-CBD fusion encoded on the plasmid pMB914.

EXAMPLE 11

Treatment of Cotton Fabric with Pectate Lyase (SEQ ID NO: 10)

The following experiments were performed to evaluate the use of the pectate lyase of SEQ ID NO: 10 to scour textiles.

A. Materials
1) Fabric: A woven army carded cotton sateen greige, quality 428R (242 g/m²) was used.
2) Equipment: A Labomat (Mathis, Switzerland) was used at a liquor ratio of 12.5:1 (12 g fabric in 150 ml buffer/enzyme solution).
3) Pectate lyase: In Experiment 1, a pectate lyase corresponding to SEQ ID NO: 10 was used, formulated in a solution containing 0.02 M phosphate buffer and 0.4 g/L non-ionic surfactant (Tergitol 15-S-12 from Union Carbide). In Experiment 2, the pectate lyase of SEQ ID NO: 4 was used, formulated in a solution containing 0.05 M phosphate/borate buffer, in 2.0 g/L non-ionic surfactant (Tergitol 15-S-12 from Union carbide), and 1.0 g/L wetter (Dioctyl sulfosuccinate).

B. Procedures and Results

In Experiment 1, the test fabrics were contacted with the aqueous solution containing the pectate lyase for 15 minutes at temperatures ranging between 60–80° C. and pHs ranging between 7–11, after which residual pectin was quantified.

Figure 3:
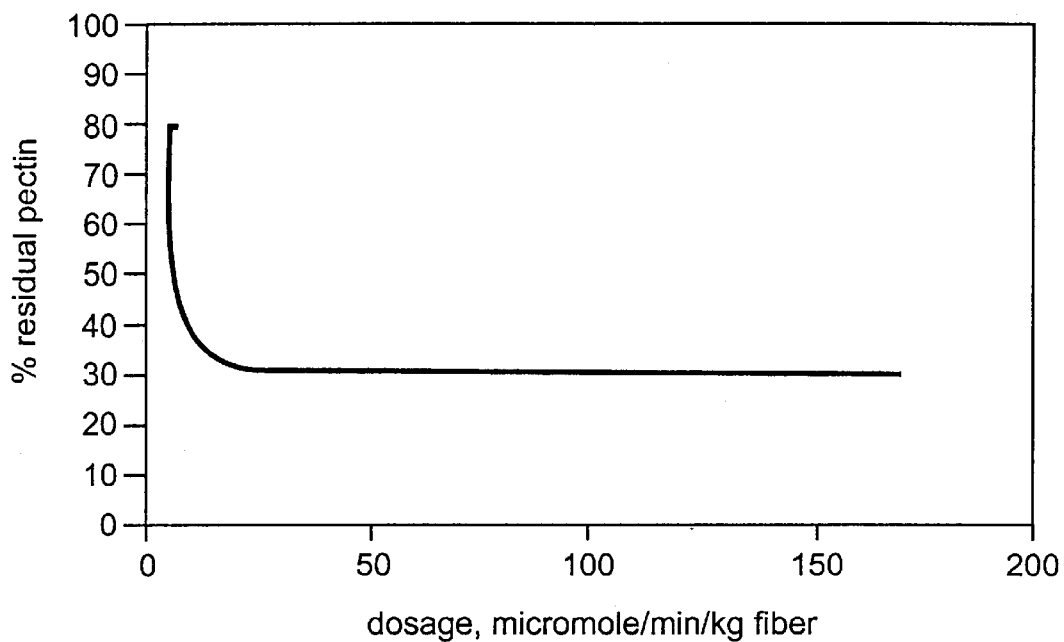
FIG. 3 is a graphic illustration of the effect of the dosage of thermostable pectate lyase on removal of pectin from a cotton fabric. The removal of pectin is expressed as % residual pectin, and the dosage as micromol/min/kg fiber. The pectate lyase was applied to the fabric at pH 9 and 80° C.

FIG. 3 below shows a contour plot of the % residual pectin as a function of both pH and temperature, and FIG. 3 shows the % residual pectin as a function of the enzyme dosage. The pH optimum for pectin removal was 9.2 and the temperature optimum was above 80° C. In Experiment 2, the test fabrics were contacted with the aqueous solution containing the pectate lyase at 600 APSU/kg cotton, squeezed in a roller system to give a solution pickup of 85%, and incubated for 60 minutes at temperatures between 40–70° C., after which residual pectin was quantified. The % residual pectin as a function of temperature is shown in the Table below.

| Temperature (° C.) | Residual Pectin (%) |
|---|---|
| 40° C. | 35% |
| 55° C. | 28% |
| 70° C. | 40% |

LITERATURE

Lever, M. (1972) A new reaction for colormetric determination of carbohydrates. Anal. Biochem. 47, 273–279.

N. C. Carpita and D. M. Gibeaut (1993) The Plant Journal 3:1–30.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172:4315–4321.

What is claimed is:

1. An isolated polypeptide having pectate lyase activity, which is:
   (a) a polypeptide having an amino acid sequence that is at least 95% identical to the sequence of amino acids 28–341 of SEQ ID NO: 4;
   (b) a polypeptide encoded by a nucleic acid that hybridize with the sequence of nucleotides 82–1026 of SEQ ID NO: 3 under hybridization conditions comprising hybridization in SXSSC at 45° C. and washing in 2XSSC at 75° C.

2. The polypeptide of claim 1, which has an amino acid sequence that is at least 95% identical to the sequence of amino acids 28–341 of SEQ ID NO: 4.

3. The polypeptide of claim 2, which has an amino add sequence that is at least 98% Identical to the sequence of amino acids 28–41 of SEQ ID NO: 4.

4. The polypeptide of claim which is encoded by a nucleic acid that hybridizes with the sequence of nucleotides 82–1026 of SEQ ID NO: 3 under hybridization conditions comprising 5XSSC at 45° C. and washing In 2XSSC at 75° C.

5. A detergent composition comprising a polypeptide of claim 1 and a surfactant.

6. A process for cleaning a surface, comprising treating the surface with a cleaning solution containing a polypeptide of claim 1.

7. A process for machine treatment of a fabric, comprising treating the fabric during a washing cycle of a machine washing process with a washing solution containing a polypeptide of claim 1.

8. A method for improving the properties of cellulosic fibers, yarn, woven or non-woven fabric, comprising treating the fibers, yarn or fabric with an effective amount of a polypeptide of claim 1.

9. A method for degradation or modification of plant material, comprising treating the plant material with an effective amount of a polypeptide of claim 1.

10. claim A method for animal feed, comprising adding an effective amount of a polypeptide of claim 1 as an animal feed additive to conventional animal feed ingredients.

11. A method for processing wins or juice, comprising treating the wine or juice with an effective amount of a polypeptide of claim 1.

12. A fused polypeptide comprising a polypeptide of claim linked to one or more cellulose binding domains.

13. The polypeptide of claim 12, wherein the cellulose binding domain is obtained from *Clostridium thermocellum* strain YS.

* * * * *